United States Patent
Ying et al.

(10) Patent No.: US 11,142,790 B2
(45) Date of Patent: Oct. 12, 2021

(54) MICROFLUIDIC DEVICE

(71) Applicant: AGENCY FOR SCIENCE, TECHNOLOGY AND RESEARCH, Singapore (SG)

(72) Inventors: Jackie Y. Ying, Singapore (SG); Guolin Xu, Singapore (SG); Rensheng Deng, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 555 days.

(21) Appl. No.: 15/302,974

(22) PCT Filed: Mar. 30, 2015

(86) PCT No.: PCT/SG2015/050054
§ 371 (c)(1),
(2) Date: Oct. 7, 2016

(87) PCT Pub. No.: WO2015/156738
PCT Pub. Date: Oct. 15, 2015

(65) Prior Publication Data
US 2017/0029871 A1    Feb. 2, 2017

(30) Foreign Application Priority Data

Apr. 9, 2014 (SG) .......................... 10201401377X

(51) Int. Cl.
*C12Q 1/68* (2018.01)
*G01N 21/64* (2006.01)
(Continued)

(52) U.S. Cl.
CPC ............ *C12Q 1/686* (2013.01); *B01L 3/5027* (2013.01); *B01L 3/50273* (2013.01);
(Continued)

(58) Field of Classification Search
CPC ............ B01L 3/5027; B01L 2200/027; B01L 2200/0642; B01L 2200/0673;
(Continued)

(56) References Cited

U.S. PATENT DOCUMENTS 8,343,443 B2    1/2013  Ying et al.
2011/0124132 A1*  5/2011  Kim ..................... B01L 3/50273
                                                        436/525
(Continued)

FOREIGN PATENT DOCUMENTS

CN        102004145       4/2011
EP        1 985 366 A2    10/2008
(Continued)

OTHER PUBLICATIONS

PCT Notification of Transmittal of the International Search Report and the Written Opinion of the International Searching Authority, or the Declaration for PCT Counterpart Application No. PCT/SG2015/050054, 15 pp., (dated Jun. 22, 2015).
(Continued)

*Primary Examiner* — Rebecca M Fritchman
(74) *Attorney, Agent, or Firm* — Womble Bond Dickinson (US) LLP

(57) ABSTRACT

There is provided a microfluidic device comprising: a plurality of wells, each well comprising one opening to function as an inlet and an outlet for the well, wherein each opening is in fluid communication with a common fluidic channel, and wherein each opening is connected to the common fluidic channel via an isolation channel, and wherein the plurality of wells is arranged on the device in a radially symmetrical pattern. There is also provided a system and method comprising the device.

17 Claims, 9 Drawing Sheets

(51) Int. Cl.
  *C12Q 1/686* (2018.01)
  *B01L 3/00* (2006.01)
  *G01N 33/543* (2006.01)
(52) U.S. Cl.
  CPC ... *B01L 3/502715* (2013.01); *B01L 3/502738* (2013.01); *B01L 3/502746* (2013.01); *G01N 21/6452* (2013.01); *G01N 33/54366* (2013.01); *B01L 2200/027* (2013.01); *B01L 2200/0642* (2013.01); *B01L 2200/0673* (2013.01); *B01L 2200/0684* (2013.01); *B01L 2200/0689* (2013.01); *B01L 2200/10* (2013.01); *B01L 2200/12* (2013.01); *B01L 2200/142* (2013.01); *B01L 2300/0627* (2013.01); *B01L 2300/0803* (2013.01); *B01L 2300/0816* (2013.01); *B01L 2300/0829* (2013.01); *B01L 2300/0864* (2013.01); *B01L 2300/168* (2013.01); *B01L 2300/18* (2013.01); *B01L 2400/049* (2013.01); *B01L 2400/084* (2013.01); *G01N 2021/6482* (2013.01)
(58) Field of Classification Search
  CPC ......... B01L 2200/10; B01L 2300/0803; B01L 2300/0816; B01L 2300/0864; B01L 2400/049; B01L 2300/0829; B01L 2300/0627; B01L 2200/142; B01L 2200/12; B01L 2200/0689; B01L 2200/0684; B01L 3/502738; B01L 3/50273; B01L 3/502715; B01L 2400/084; B01L 2300/18; B01L 2300/168; B01L 3/502746; G01N 21/6452; G01N 2021/6482; G01N 33/54366; C12Q 1/686
  See application file for complete search history.

(56) References Cited

U.S. PATENT DOCUMENTS

2013/0137105 A1* 5/2013 Zhang ............... C12P 19/34
  435/6.12
2016/0107159 A1* 4/2016 Gong .................. B01L 3/5027
  435/6.12

FOREIGN PATENT DOCUMENTS

EP  2 277 624 A2  1/2011
WO  2015057165 A1  4/2015

OTHER PUBLICATIONS

Qi, H., "Polymer Based Continuous-Flow PCR Microfluidic Chip System and Its Application," China Knowledge Resource Integrated Database, Jul. 16, 2009, 8 pgs., Beijing University of Technology.
Bhattacharya, et al., "PCR-based detection in a micro-fabricated platform," Lab Chip, 2008, pp. 1130-1136, vol. 8, The Royal Society of Chemistry.
Cooney, et al., "A plastic, disposable microfluidic flow cell coupled on-chip PCR and microarray detection of infectious agents," Biomed Microdevices, 2012, pp. 45-53, vol. 14, Springer Science+Business Media.
Crevillen, et al., "Real sample analysis on microfluidic devices," Talanta, 2007, pp. 342-357, vol. 74, Elsevier.
Dettloff, et al., "Nucleic Acid Amplification of Individual Molecules in a Microfluidic Device," Analytical Chemistry, 2008, pp. 4208-4213, vol. 80, American Chemical Society.
Fang, et al., "Real-time PCR microfluidic devices with concurrent electrochemical detection," Biosensors and Bioelectronics, 2009, pp. 2131-2136, vol. 24, Elsevier.
Focke, et al., "Centrifugal microfluidic system for primary amplification and secondary real-time PCR," Lap Chip, 2010, pp. 3210-3212, vol. 10, The Royal Society of Chemistry.
Focke, et al., "Lab-on-a-Foil: microfluidics on thin and flexible films," Lab Chip, 2010, pp. 1365-1386, vol. 10, The Royal Society of Chemistry.
Focke, et al., "Microstructuring of polymer films for sensitive genotyping by real-time PCT on a centrifugal microfluidic platform," Lab Chip, 2010, pp. 2519-2526, vol. 10, The Royal Society of Chemistry.
Gong, et al., "Microfluidic handling of PCR solution and DNA amplification on a reaction chamber array biochip," Biomed Microdevices, 2006, pp. 167-176, vol. 8, Springer Science+Business Media, LLC.
Gulliksen, et al., "Real-Time Nucleic Acid Sequence-Based Amplification in Nanoliter Volumes," Analytical Chemistry, 2004, pp. 9-14, vol. 76, No. 1, American Chemical Society.
Guttenberg, et al., "Planar chip device for PCR and hybridization with surface acoustic wave pump," Lab Chip, 2005, pp. 308-317, vol. 5, The Royal Society of Chemistry.
Haeberle, et al., "Microfluidic platforms for lab-on-a-chip applications," Lab Chip, Oct. 2007, 25 pages, The Royal Society of Chemistry.
Jia, et al., "A low-cost, disposable card for rapid polymerase chain reaction," Colloids and Surfaces B: Biointerfaces, 2007, pp. 52-60, vol. 58, Elsevier.
Laser, et al., "A review of micropumps," Journal of Micromechanics and Microengineering, 2004, pp. R35-R64, vol. 14, Institute of Physics Publishing Ltd.
Lee, et al., "Diagnostic Testing for Pandemic Influenza in Singapore," Journal of Molecular Diagnostics, Sep. 2010, pp. 636-643, vol. 12, No. 5, American Society for Investigative Pathology and the Association for Molecular Pathology.
Madou, et al., "Lab on a CD," Annual Review of Biomedical Engineering, 2006, pp. 601-628, vol. 8, Annual Reviews.
Marcus, et al., "Parallel Picoliter RT-PCR Assays Using Microfluidics," Analytical Chemistry, 2006, pp. 956-958, vol. 78, No. 3, American Chemical Society.
Morrison, et al., "Nanoliter high throughput quantitiative PCR," Nucleic Acids Research, 2006, 9 pgs., vol. 34, No. 18, The Author(s).
Neuzil, et al., "Disposable real-time microPCR device: lab-on-a-chip at a low cost," Molecular Biosystems, 2006, pp. 292-298, vol. 2, The Royal Society of Chemistry.
Neuzil, et al., "Ultra fast miniaturized real-time PCR: 40 cycles in less than six minutes," Nucleic Acids Research, 2006, 9 pgs., vol. 34, No. 1, The Author(s).
Oh, et al., "A review of microvalves," Journal of Micromechanics and Microengineering, 2006, pp. R13-R39, vol. 16, Institute of Physics Publishing.
Ramalingam, et al., "Real-time PCR-based microfluidic array chip for simultaneous detection of multiple waterborne pathogens," Sensors and Actuators B, 2010, pp. 543-552, vol. 145, Elsevier.
Ramalingam, et al., "Real-time PCR array chip with capillary-driven sample loading and reactor sealing for point-of-care applications," Biomed Microdevices, 2009, pp. 1007-1020, vol. 11, Springer Science + Business Media, LLC.
Trung, et al., "Multi-chamber PCR chip with simple liquid introduction utilizing the gas permeability of polydimethyisiloxane," Sensors and Actuators B: Chemical, 2010, pp. 284-290, vol. 149, Elsevier.
Wang, et al., "A miniturized quantitative polymerase chain reaction system for DNA amplification and detection," Sensors and Actuators B: Chemical, 2009, pp. 329-337, vol. 141, Elsevier.
Xu, et al., "A self-contained all-in-one cartridge for sample preparation and real-time PCR in rapid influenza diagnosis," Lap Chip, 2010, pp. 3103-3111, vol. 10, The Royal Society of Chemistry.
Xu, et al., "A self-contained polymeric cartridge for automated biological sample preparation," Biomicrofluidics, 2011, 9 pages, vol. 5, American Institute of Physics.
Yao, et al., "Micro Flow-through PCR in a PMMA Chip Fabricated by KrF Excimer Laser," Biomedical Microdevices, 2005, pp. 253-257, vol. 7, No. 3, Springer Science + Business Media, Inc.

(56) References Cited

OTHER PUBLICATIONS

Zhang, et al., "PCR microfluidic devices for DNA amplification," Biotechnology Advances, 2006, pp. 243-284, vol. 24, Elsevier.

Pjescic, et al., "Glass-composite prototyping for flow PCR with in situ DNA analysis," Biomed Microdevices, 2010, pp. 333-343, vol. 12, Springer.

Dimov, et al., "Integrated microfluidic tmRNA purification and real-time NASBA device for molecular diagnostics," Lab Chip, 2008, pp. 2071-2078, vol. 8, No. 12.

Gulliksen, et al., "Parallel nanoliter detection of cancer markers using polymer microchips," Lab Chip, 2005, pp. 416-420, No. 5, vol. 4.

Nisar, et al., "MEMS-based micropumps in drug delivery and biomedical applications," Sens Actuators B Chem, 2008, pp. 917-942, vol. 130, No. 2.

Liu, et al., "Self-contained, fully integrated biochip for sample preparation, polymerase chain reaction amplification, and DNA microarray detection," Analytical Chemistry, 2004, pp. 1824-1831, vol. 76, No. 7.

Herbert, et al., "Increase PCR sensitivity by using paraffin wax as a reaction mix overlay," Mol Cell Probes, 1993, pp. 249-252, vol. 7, No. 3.

Asiello, et al., "Miniaturized isothermal nucleic acid amplification, a reivew," Lab Chip, 2011, pp. 1420-1430, vol. 11, No. 8.

Wu, et al., "Detection of dengue viral RNA using a nucleic acid sequence-based amplification assay," J Clin Microbiol, 2001, pp. 2794-2798, vol. 39, No. 8.

Mori, et al., "Real-time turbidimetry of LAMP reaction for quantifying template DNA," J Biochem Biophys Methods, 2004, pp. 145-157, vol. 59, No. 2.

Chow, et al., "Application of isothermal helicase-dependent amplification with a disposable detection device in a simple sensitive stool test for toxigenic Clostridium difficile," J Mol Diagn, 2008, pp. 452-458, vol. 10, No. 5.

Lam, et al., "Loop-mediated isothermal amplification of a single DNA molecule in polyacrylamide gel-based microchamber," Biomed Microdevices, 2008, pp. 539-546, vol. 10, No. 4.

\* cited by examiner

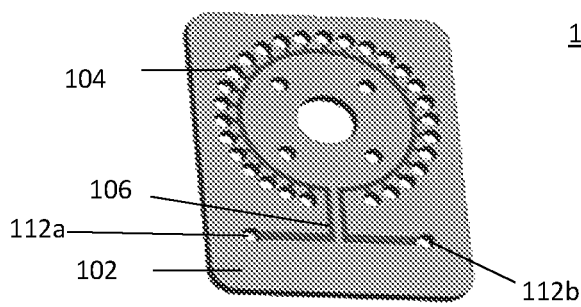 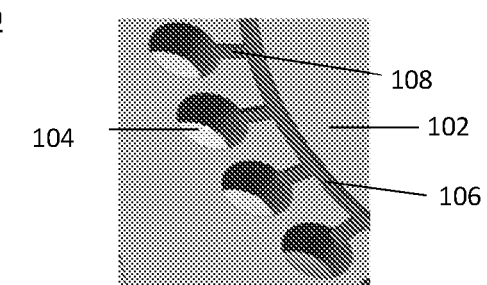
Fig. 1a  Fig. 1b
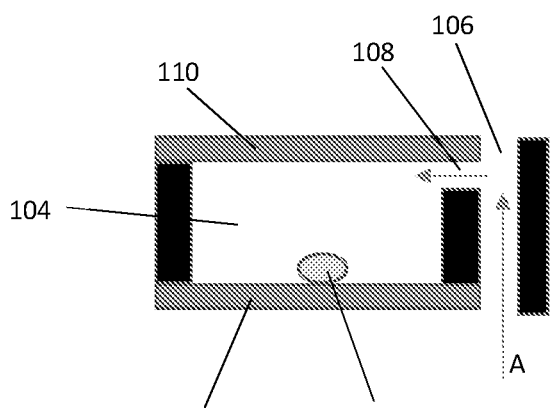
Fig. 1c
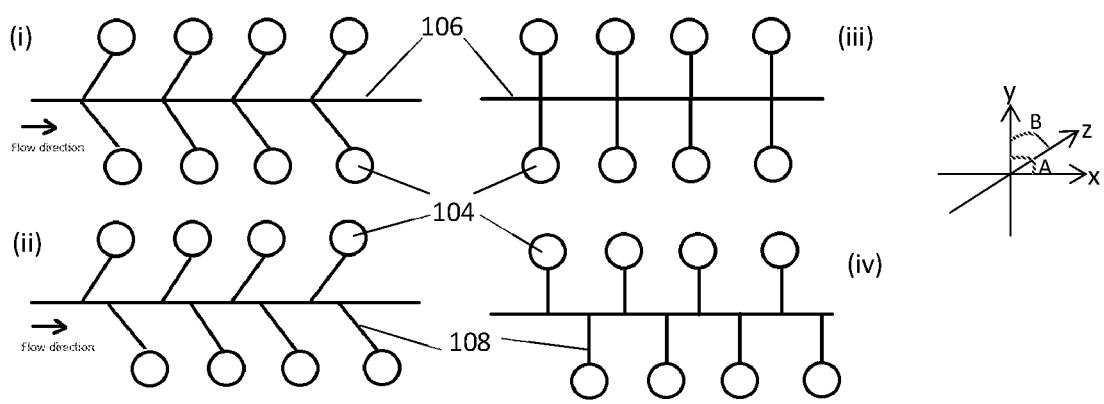
Fig. 1d

MICROFLUIDIC DEVICE

CROSS-REFERENCE TO RELATED APPLICATIONS

This patent application is a U.S. National Phase Application under 35 U.S.C. § 371 of International Application No. PCT/SG2015/050054, filed Mar. 30, 2015, entitled MICROFLUIDIC DEVICE, which claims the benefit of priority of Singapore Patent Application No. 10201401377X, filed Apr. 9, 2014, the contents of which were incorporated by reference in their entirety for all purposes.

FIELD OF THE INVENTION

The present invention relates to the field of biochemical and biomedical engineering, in particular microfluidic devices and microfluidic devices for detection of biochemical molecules.

BACKGROUND OF THE INVENTION

Polymerase chain reaction (PCR) is a well-developed method for nucleic acid amplification and gene detection. This method is usually conducted in devices such as PCR tubes and well plates. However, microfluidic chip-based PCR devices have been increasingly researched for various applications, including food safety testing, environmental monitoring and point-of-care clinical diagnostics. Compared to conventional devices, the microfluidic/nanofluidic chip-based PCR systems provide many advantages, such as rapid operation, small sample volume, ease of sample transport to analytical stage, and parallel amplification in multiple wells. One such example of a microfluidic PCR device is a lab-on-cartridge system with three PCR reaction wells. To further enhance the detection capability of this example system, a PCR chip with many more wells has been developed, in an effort to meet the needs of applications, such as cancer and infectious disease diagnosis, wherein there could be more than 10 targets.

Microfluidic PCR platforms can be classified into three categories: chamber-stationary PCR systems, continuous-flow PCR systems and thermal convection-driven PCR systems. Among them, the chamber-stationary PCR system is most suitable for multi-chamber PCR amplification with high throughput. However, there are quite a number of challenges to overcome to effectively conduct PCR on a single chip. For example, it is not easy to uniformly deliver a small amount of PCR mixture to individual chambers. Further, as the PCR chambers have very small volumes, it would be important to prevent loss of reaction mixture by evaporation at high temperatures (for example, 95° C.). In addition, bubbles may form during the PCR process, which can significantly affect the chip operation and reduce PCR efficiency. The most commonly used method to address these issues is the integration of pumps and valves onto a chip for PCR mixture loading and sealing. However, integration of many components onto a single chip complicates device fabrication and operation.

An alternative method is to utilize capillary-driven microfluidics for the loading of sample into the reaction chambers, which can be achieved by using surfactants to minimize the contact angle between the PCR mixture and the PCR chip. However, the surfactants added often have undesirable effects on PCR amplification efficiency. Centrifugal force is another option since it is easy to be applied to disk-type microfluidic device for accurate PCR mixture delivery. However, fluidic transfer based on centrifugal force is not flexible, especially when the PCR portion is integrated with other bio-sample preparation components.

Different methods for rapid PCR filling have been developed. For example, a PCR array chip has been developed that automatically sucked the PCR mixture into the distribution channels and reaction wells by silanizing the surfaces of channels/wells to enhance the capillary force for driving fluid. However, additional steps are required in this method to condition the surfaces.

Preventing loss of PCR mixture is a challenge for microfluidics-based PCR systems. The three main causes for sample loss are as follows. (i) Air trapped in reaction wells during sample loading expands under high temperatures, and pushes the sample solution out of the wells. Several methods have been developed to avoid the trapping of air, including improvement of the design of PCR well shape and modifying the well surface to render it highly hydrophilic. (ii) The gas originally dissolved in the PCR mixture is released under high temperatures due to its reduced solubility; this can also push the sample solution out of the wells. De-gasification of the PCR mixture before loading can help to minimize this effect. (iii) The PCR mixture will evaporate at high temperatures, leading to the loss of sample volume; this is especially significant after multiple thermal cycles. In order to resolve this problem, individual valves are used to seal the reaction chambers after filling them.

Further, rapid detection of various bacteria is critical for food safety testing and clinical diagnosis. Conventional PCR or reverse transcription PCR (RT-PCR) is commonly used for bacteria detection. However, it suffers from one important drawback, i.e. it requires rapid and precise thermal cycling for the denaturation, extension and annealing of target DNA molecules during the reaction processes.

There is therefore a need to provide a microfluidic device and system that overcomes, or at least ameliorates, one or more of the disadvantages described above.

SUMMARY OF THE INVENTION

In a first aspect, there is provided a microfluidic device comprising: a plurality of wells, each well comprising one opening to function as an inlet and an outlet for the well, wherein each opening is in fluid communication with a common fluidic channel, and wherein each opening is connected to the common fluidic channel via an isolation channel, and wherein the plurality of wells is arranged on the device in a radially symmetrical pattern.

In a second aspect, there is provided a system comprising: a microfluidic device as disclosed herein; a detection device arranged above or below the microfluidic device for detecting a signal emitted by a possible reaction product comprised in the wells during use.

In a third aspect, there is provided a method of detecting at least one target molecule from a liquid sample using the system as disclosed herein, wherein the method sequentially comprises: (i) filling the plurality of wells with the liquid sample from the source comprising the target molecule; (ii) filling the common fluidic channel with the sealant from the sealant source; (iii) allowing a reaction between the detection probe and the target molecule to take place in the plurality of wells; (iv) detecting a signal emitted by the reaction product.

BRIEF DESCRIPTION OF THE DRAWINGS

The invention will be better understood with reference to the detailed description when considered in conjunction with the non-limiting examples and the accompanying drawings, in which:

FIG. 1 shows a schematic diagram of a device in accordance with an embodiment of the present disclosure. Specifically, FIG. 1a shows a schematic overview of the device 100, FIG. 1b shows a magnified schematic of device 100 and FIG. 1c. shows a cross-section of well 104. FIG. 1d shows another example, wherein the plurality of wells 104 is positioned on the device 100 in a linear pattern, the wells being in fluid communication with one common fluidic channel 106 via isolation channels 108.

FIG. 6a shows a photo of the PCR chamber when an insufficient vacuum volume of less than 5 mL was used, while FIG. 6a and FIG. 6b were referred to in Example 3a.

DETAILED DESCRIPTION OF THE PRESENT INVENTION

Figure 2A:
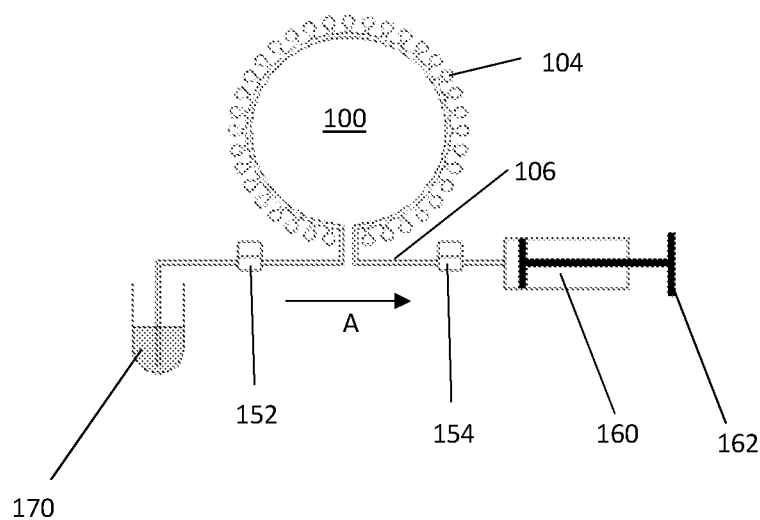
FIG. 2a shows a schematic diagram of a device in accordance with an embodiment of the present disclosure connected to a vacuum source 160 and a tube 170 as a source comprising a possible target molecule.

In an embodiment, there is provided a microfluidic device comprising: a plurality of wells, each well comprising one opening to function as an inlet and an outlet for the well, wherein each opening is in fluid communication with a common fluidic channel, and wherein each opening is connected to the common fluidic channel via an isolation channel, and wherein the plurality of wells is arranged on the device in a radially symmetrical pattern.

The disclosed device may be a simple device which does not involve many components. Accordingly, the manufacture of the device may be economical and operation of the device is easy. Further, the disclosed device may improve the speed and accuracy of delivery and sealing of reaction mixture.

The disclosed device may comprise a plurality of wells in numbers as required by the application. For example, the device may comprise a range of about 2 to 100 wells, or about 5 to 100 wells, or about 10 to 100 wells, or about 20 to 100 wells, or about 5 to 50 wells, or about 10 to 50 wells, or 26 wells, or 28 wells. In some instances, the disclosed device is flexible to meet the needs of various applications.

The diameter and the depth of each well may be adjusted to suit the application of the device. The volume of each well may be precisely controlled. In instances, it may be essential to reduce the volume of the well.

The well may have a shape suitable to contain a reaction mixture, such as a sphere or a cube or a bulb. Each well may have different dimensions or shapes.

The volume of each well may be between about 1 μL to 50 μL, or about 2 μL to 50 μL, or about 3 μL to 50 μL, or about 2 μL to 10 μL, or about 3 μL to 10 μL, or any value falling within these ranges. The total liquid volume comprised in the device may be between about 2 μL to 1000 μL, or about 10 μL to about 200 μL, or about 10 μL to about 150 μL, or about 20 μL to about 200 μL, or about 20 μL to about 150 μL, or about 30 μL to about 200 μL, or about 30 μL to about 150 μL, or about 30 μL to about 100 μL. In an example, the volume of the well is precisely controlled to be 2.99 to 3.09 μL. In an example, the total liquid volume of the disclosed device may be a fraction of that required in prior art devices. For example, the total liquid volume of the disclosed device having 10 wells is about 20% of the total volume required in 10 conventional PCR tubes. The total liquid volume may further be reduced by re-introducing the excess liquid that was removed from the entry channel. The total liquid volume here includes the volume of the wells and the volume of the liquid in the entry channel.

The diameter of the well may be between about 1 mm to 4 mm, or about 1.5 mm to 4 mm, or about 1.7 mm to 4 mm, or about 2 mm to 4 mm, or about 2.2 mm to 4 mm, or about 2.5 mm to 4 mm, or about 3 mm to 4 mm, or about 1 mm to 3 mm, or about 1 mm to 2.5 mm, or about 1 mm to 2.2 mm, or about 1 mm to 2 mm, or about 1.5 mm to 3 mm, or about 2 mm to 3 mm, or about 2 mm to 2.5 mm. The depth or height of the well may be between about 0.5 mm to 1.5 mm, or about 0.6 mm to 1.5 mm, or about 0.7 mm to 1.5 mm, or about 0.8 mm to 1.5 mm, or about 0.9 mm to 1.5 mm, or about 1 mm to 1.5 mm, or about 0.5 mm to 1 mm, or about 0.5 mm to 0.9 mm, or about 0.5 mm to 0.8 mm, or about 0.8 mm to 1 mm. In an example, the diameter of the well may be reduced to about 2 mm and the depth of the well may be reduced to about 1 mm to reduce the volume of the well to about 3 µL.

As used herein, the term "diameter" refers to the maximum length of an object. For objects having an irregular shape, the diameter is the length of the longest cross section of the object.

Each well comprises one opening. The opening allows access into the well, as well as an exit from the well. In an example, the opening may function as either an entrance or an exit at any one given time. Liquid enters the well through the opening of the well. The opening of the well may lead to the isolation channel. Therefore, the opening may be of the same dimensions as the isolation channel, or may be of different dimensions as the isolation channel so long as liquid flow is not impeded.

The isolation channel may be positioned at the top of the well, or at the middle of the well, or at the bottom of the well, as required. That is, the isolation channel may allow liquid to enter the top of the well, or at the middle of the well, or at the bottom of the well.

In an example, liquid may be allowed to enter the well quickly. In cases where the device is used for reactions, this example aids in providing faster delivery of reaction mixtures into the wells to start the reaction. In instances, liquid in the well may be completely or partially prevented from exiting the well. The isolation channel may be sized accordingly.

The isolation channel may have any cross-sectional shape. The cross-sectional shape of the isolation channel may be chosen to completely or partially prevent liquid in the well from exiting the well, while allowing liquid to enter the well. For example, the cross-sectional shape of the isolation channel may be a cone-shaped cross-section or a circular cross-section or a square-shaped cross-section. In an example, the width of the isolation channel may be between about 0.05 mm to about 3 mm. The depth of the isolation channel may be between about 0.05 mm to about 3 mm. Where the cross-section of the isolation channel is circular, the diameter may be between about 0.05 mm to about 3 mm. In an example, the cross-sectional dimension of the isolation channel may be between about 0.05 and 3 mm by between about 0.05 and 3 mm. In another example, the cross-sectional dimension of the isolation channel may be about 0.5 mm by 0.5 mm.

Liquid enters the well from the common fluidic channel. The common fluidic channel may have any cross-sectional shape. The cross-sectional shape of the fluidic channel may be chosen so as not to impede liquid flow, such as for example a circular cross-section or a square-shaped cross-section. In an example, the width of the fluidic channel may be between about 0.05 mm to about 3 mm. The depth of the fluidic channel may be between about 0.05 mm to about 3 mm. Where the cross-section of the fluidic channel is circular, the diameter may be between about 0.05 mm to about 3 mm. In an example, the cross-sectional dimension of the fluidic channel may be between about 0.05 and 3 mm by between about 0.05 and 3 mm. In another example, the cross-sectional dimension of the fluidic channel may be about 0.5 mm by 0.5 mm. If the channel is too small, e.g. smaller than the dimensions disclosed, the filling of the wells may be impeded. On the other hand, if the channel is too big, e.g. bigger than the dimensions disclosed, reagents may be wasted.

One or both ends of the common fluidic channel may be open-ended. The open end(s) of the fluidic channel may have a width or depth or diameter of between about 0.05 mm to about 3 mm. In an example, the diameter of the fluidic channel may be about 1 mm.

Figure 5A:
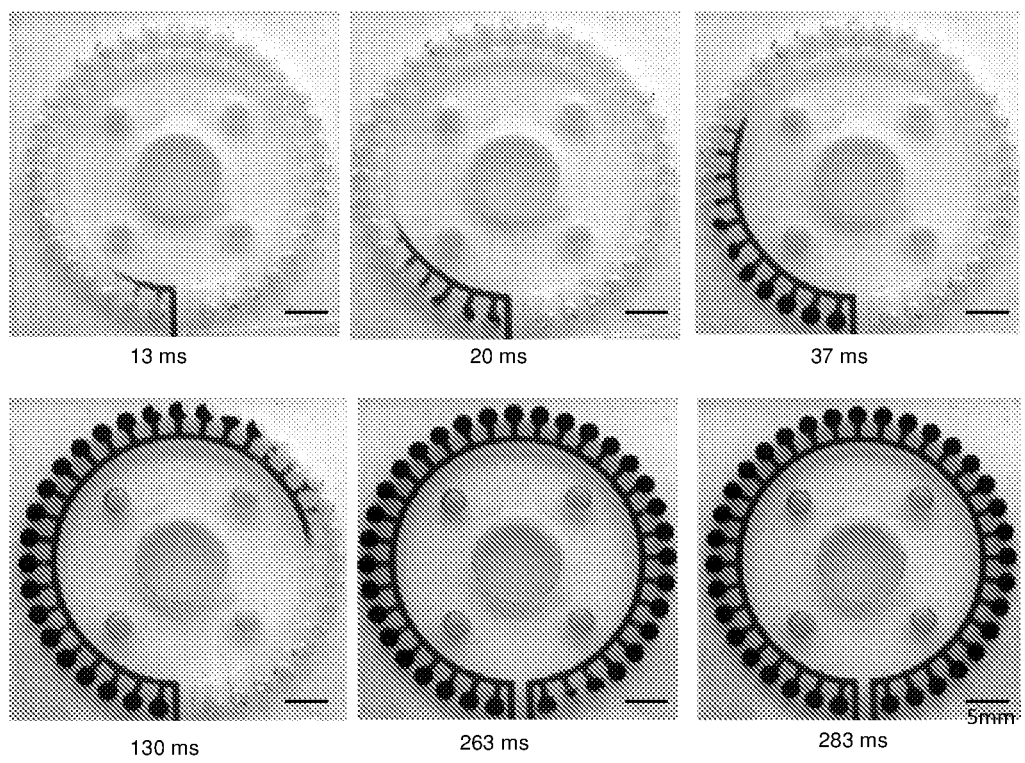
FIG. 5a shows photos of the sample loading into device 100, referred to in Example 2.

In instances, at least some or all of the plurality of wells are in fluid communication with the common fluidic channel. In instances, liquid from the common fluidic channel may enter the wells sequentially. In one example, liquid may completely fill a first well connected to the common fluidic channel along the direction of liquid flow, and overflow from the first well into the common fluidic channel to fill the next well. In another example, many wells can be filled simultaneously while the liquid is in the common fluidic channel, as shown in FIG. 5a.

The term "fluid communication" as used herein may refer to the communication of liquid or gas. The liquid referred to herein may be a solution, such as an aqueous solution, or a mixture, such as a reaction mixture.

The plurality of wells is arranged on the device in a manner so that all of the wells may be substantially uniformly detectable. As will be described in further detail below, each well may comprise a detection probe capable of forming a reaction product with a target molecule. The reaction product may emit a signal which the detection device of the disclosed system detects, by, e.g. illuminating light on the plurality of wells. In instances, the plurality of wells is arranged on the device in a complementary manner to the detection mode, so that detection of a possible reaction product can be substantially uniform.

In an embodiment, the plurality of wells is arranged on the device in a radially symmetrical pattern. As used herein, the term "radial symmetry", or grammatical variants thereof, refers to an arrangement of constituents which is symmetrical about a particular axis. In some examples, the arrangement of constituents is symmetrical about more than three axes, wherein the axes intersect at a central point.

In an example, the plurality of wells may be positioned on the device in a circular arrangement or arranged on the device in a circular loop. The common fluidic channel connecting the plurality of wells may form the shape of "Ω" and hence, may be referred to as an "Omega PCR array chip". FIG. 1a shows an example of this embodiment. In another example shown in FIG. 1d, the plurality of wells may be positioned on the device in a linear pattern, wherein the wells are in fluid communication with one common fluidic channel.

The term "chip" as used herein refers to a substrate generally comprising a microfluidic device, such as the disclosed device, comprising a multitude of channels and chambers that may or may not be interconnected with each another. Typically, such chips include a multitude of active or passive components such as channels, valves, pumps, and related control systems.

The plurality of wells may be positioned on either side of the common fluidic channel. In an example, all of the plurality of wells may be located on one side of the fluidic channel in a common plane. Where the plurality of wells is arranged in a circular loop, all of the plurality of wells may be located on the outer periphery of the loop. In another example, a first set of wells may be positioned on a first side of the fluidic channel, while a second set of wells may be positioned on the opposite side of the fluidic channel along a y-axis in a common plane as the first side, as shown in FIG. 1d. In yet another example, one set or all of the wells may be positioned anywhere radially around the axis through the common fluidic channel at an angle B, e.g., along a z-axis wherein in angle B is 90°. Each well may be positioned at an angle of between about 10° and about 90°, or 45°, or 90°, relative to the common fluidic channel. The isolation channel of each well may be displaced at an angle A of between about 10° and about 90°, or 45° (as shown in (i) and (ii) of FIG. 1d), or 90° (as shown in (iii) and (iv) of FIG. 1d), relative to the common fluidic channel. Where the plurality of wells is positioned on different sides of the common fluidic channel, the isolation channels of the opposing wells may be located at the same point on the common fluidic channel (as shown in (i) and (iii) of FIG. 1d). For example, a point on the common fluidic channel leads to two isolation channels, one isolation channel on the positive y-axis and another isolation channel on the negative y-axis, where the x-axis is an axis parallel to the common fluidic channel. In another example, the isolation channels of opposing wells are located at different or staggered points on the common fluidic channel (as shown in (ii) and (iv) of FIG. 1d). For example, a point on the common fluidic channel leads to one isolation channel on the positive y-axis and another point on the common fluidic channel leads to another isolation channel on the negative y-axis, where the x-axis is an axis parallel to the common fluidic channel.

An example of the disclosed device in accordance with an embodiment of the present disclosure is shown in FIGS. 1a, 1b and 1c. FIG. 1 shows a schematic overview of device 100. FIG. 1b shows a magnified schematic of device 100. FIG. 1c shows a cross-section of well 104.

Device 100 comprises substrate 102 comprising a plurality of holes 104 to be enclosed by optical adhesive films 110 on the top and bottom (shown in FIG. 1c) so that the holes 104 function as wells. Accordingly, device 100 has a "sandwich" structure. Substrate 102 is made of polycarbonate (PC) having 1.5 mm in thickness. Two optical adhesive films 110 having 0.1 mm in thickness are used to seal the top and bottom of the substrate 102, forming enclosed well 104. Device 100 contains 26 wells, uniformly located outside a circular common fluidic channel 106. Each well 104 has a diameter of 2.0 mm and a depth of 1.0 mm, corresponding to a sample volume of about 3 µL. The wells are linked to the common fluidic channel 106 via an isolation channel 108 of 0.5 mm in width and 0.5 mm in depth. The common fluidic channel 106 for delivering liquid to individual wells 104 has a width and a depth of 0.5 mm and 0.5 mm, respectively. At both ends of the common fluidic channel 106, there are two holes 112a, 112b of 1 mm in diameter, which are to be connected with inlet and outlet tubes, respectively (not shown). Liquid is delivered into well 104 from 112a and in the direction shown by arrow A. FIG. 1c shows well 104 pre-loaded with primer 114.

A first end of the common fluidic channel may be configurable to fluidly connect with fluid(s) that are to be introduced into the device. The fluids introduced into the device depend on the application of the device. Where the device is to be used to conduct polymerase chain reactions, the first end of the common fluidic channel may be configurable to fluidly connect with one or more of the following: a source comprising a possible target molecule, a sealant source, a washing reagent source and other sources for reagents used for polymerase chain reactions. The first end of the common fluidic channel may also be configurable to fluidly connect with a positive pressure source to aid in the introduction of the fluids. If more than one source is to be connected to the first end of the fluidic channel, the connections may be branched and may converge at the first end of the fluidic channel. In another example, each source may be connected to the first end directly or may be connected to branched connections before converging at the first end of the fluidic channel.

A second end of the common fluidic channel may be configurable to fluidly connect with a vacuum source. The vacuum source may be connected to the second end directly or may be connected to branched connections before converging at the second end of the fluidic channel. The vacuum produced by the vacuum source may aid in the drawing or pulling of fluids from the first end of the fluidic channel to the second end of the fluidic channel. If more than one source is to be connected to the first end of the fluidic channel, the connections may be branched and may converge at the first end of the fluidic channel.

In other words, the first end of the fluidic channel may be configured to push fluids into the channel and the second end may be configured to pull fluids through the channel.

Each branch or each connection from the various sources may be individually controllable by one or more valves.

In instances where an end of the fluidic channel is to be connected to a source either directly or through branches, one or more valves may be provided to regulate the flow of the source or to switch between different branches. In instances where an end of the fluidic channel is to be connected to more than one source, wherein each source is connected either directly or through branches, one or more valves may be provided on each connection to regulate the flow of the source or to switch between different branches.

The valves may be electromagnetic or rotary valves. The control of the valves may be automated, thereby facilitating the transport of the various fluids within the device. The vacuum source may be automated to provide predefined vacuum pressures. The vacuum source may be linked to the valves by a feedback loop. Thus, the disclosed device, system and method may be fully automated.

Liquid may be prevented from contacting the vacuum source. Accordingly, in some instances, one or more liquid flow stoppers are connected between the second end of the fluidic channel and the vacuum source. In an example, the liquid flow stopper may be located on each connection or may be located on each branch. In another example, the liquid flow stopper may be located on certain branches or on only one branch.

The liquid flow stopper may comprise holes sized to prevent liquid from passing through, but allow gas to pass through. The flow stopper may be fabricated from a material to aid in the prevention of liquid from passing through. For example, if the liquid is aqueous-based, the flow stopper may be fabricated from a hydrophobic material to repel the liquid.

A schematic diagram of an example of the disclosed device in accordance with an embodiment of the present disclosure is shown in FIG. 2a. Vacuum source 160 for drawing liquid and sealant into the common fluidic channel 106 and wells 104 of device 100 consists of a motorized-driven 10-mL syringe (NE-1000, New Era Pump Systems Inc. USA) with plunger 162, and two pinch valves (152 and 154) for turning on/off the vacuum pulled by vacuum source 160. Liquid flows in the direction of arrow A. A 200-µL Eppendorf tube 170 is used as the reservoir for holding liquid. Tube 170 is connected to the inlet of the common fluidic channel via a silicone tube (not shown). The outlet of the common fluidic channel of device 100 was connected to the syringe 160 via another silicone tube (not shown).

Figure 3:
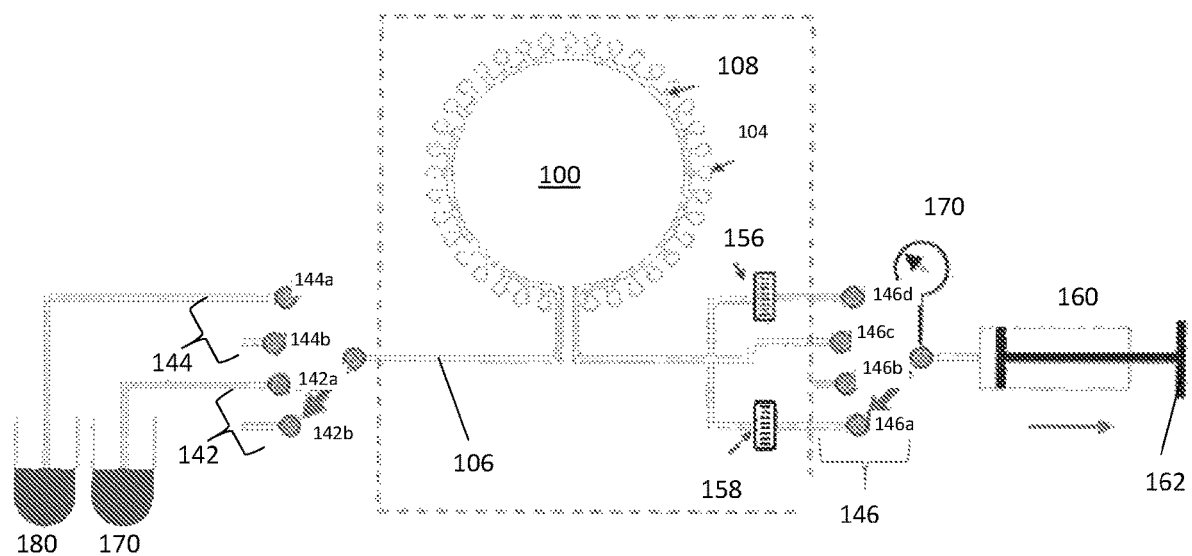
FIG. 3 shows a schematic diagram of a device in accordance with another embodiment of the present disclosure connected to a vacuum source 160, a sealant source 180 and a source 170 comprising a possible target molecule. The sources 160, 170, 180 are connected to device 100 via valves 142, 144, 146.

A schematic diagram of another example of the disclosed device in accordance with another embodiment of the present disclosure is shown in FIG. 3. In this example, the device 100 is to be fluidly connected to a source comprising a possible target molecule 170 and a sealant source 180 at the first end of the fluidic channel 106. The connection from the source 170 and the connection from the sealant source 180 converges at the first end of the fluidic channel 106. The connection from the source 170 comprises a valve 142 configurable between an "open" position 142b to allow the possible target molecule to flow from the source 170 into the first end of the fluidic channel 106 and through the fluidic channel 106; and a "close" position 142a where flow of the possible target molecule is obstructed. The connection from the sealant source 180 comprises a valve 144 configurable between an "open" position 144a to allow the sealant to flow from the source 180 into the first end of the fluidic channel 106 and through the fluidic channel 106; and a "close" position 144b where flow of the sealant is obstructed.

Still referring to FIG. 3, the vacuum source 160 is to be fluidly connected to four branches, wherein three of the four branches converge at the second end of the fluidic channel 106. The connection from the vacuum source 160 comprises a valve 146 configurable between four positions (146a, 146b, 146c, 146d) corresponding to the four branches. The first branch comprises a reagent flow stopper 158 connected between the second end of the fluidic channel 106 and the vacuum source 160 and is at valve position 146a. The second branch comprises an open ended connection and is at valve position 146b. The third branch is connected directly to the second end of the fluidic channel 106 and is at valve position 146c. The fourth branch comprises a sealant flow stopper 156 connected between the second end of the fluidic channel 106 and the vacuum source 160 and is at valve position 146d. The operation of this embodiment of device 100 will be explained in detail further below.

In instances, the device is provided in an upright position during the filling process.

In examples, each well may comprise a detection probe. The term "detection probe" generally refers to a molecule capable of binding to a target molecule, where "detection probe" may encompass probe molecules immobilized to a support or probe molecules not immobilized to a support. In an example, the detection probe is immobilized to a support including a surface, a film, or a particle. In another example, the detection probe is not immobilized to a support.

The detection probe may be capable of binding to at least a portion of the target molecule, e.g. a specific sequence of a target nucleic acid, via covalent bonding, hydrogen bonding, electrostatic bonding, or other attractive interactions, to form a reaction product. The reaction product may emit a signal which can be detected by a detection device so as to detect the presence of the target molecule, or in the case where no reaction products are formed, the absence of the target molecule. In an example, the detection probe may be a protein which binds to the target molecule which may also be a protein. Therefore, the binding in this example is via protein-protein interactions to detect, for example, a conformational change in the protein structure. In another example, the detection probe may be a nucleic acid which binds to the target molecule which may also be a nucleic acid. Therefore, the binding in this example is via hybridization so as to detect, for example, the presence or absence of a target nucleic acid or the presence of a single nucleotide mutation in the nucleic acid.

The liquid referred to herein may be a source or solution comprising the target molecule or possibly comprising the target molecule. The source comprising a possible target source may be a biological sample, e.g. a cheek swab, taken from a subject to detect the presence or absence of specific genes. The term "target nucleic acid", as used herein, refers to a nucleic acid sequence comprising a sequence region which may bind to a complementary region of the detection probe. The target nucleic acid sequence may be amplified and when hybridized with the complementary region of the detection probe, it may be possible to detect the presence or absence of the target nucleic acids and the quantitative amount of the target nucleic acids. The term "hybridization" as used in this application, refers to the ability of two completely or partially complementary single nucleic acid strands to come together in an antiparallel orientation to form a stable structure having a double-stranded region. The two constituent strands of this double-stranded structure, sometimes called a hybrid, are held together with hydrogen bonds. Although these hydrogen bonds most commonly form between nucleotides containing the bases adenine and thymine or uracil (A and T or U) or cytosine and guanine (C and G) on single nucleic acid strands, base pairing can form between bases who are not members of these "canonical" pairs. Non-canonical base pairing is well-known in the art. See e.g., The Biochemistry of the Nucleic Acids (Adams et al., eds., 1992).

The detection probe may be coupled to a detection means, such as a label, for measuring hybridization of a target to the detection probe. The label may be a radioactive isotope or a fluorophore. In an example, each detection probe may be conjugated with a different fluorophore so that the different probes can be distinguished.

In examples, the detection probe comprises DNA or RNA. In other examples, the detection probe comprises single-stranded polynucleotides having a hairpin loop structure capable of forming a double-stranded complex with a region of a sample polynucleotide. In an example, the detection probe may be a primer or a molecular beacon (MB) probe comprising a fluorophore and a quencher. In an example, the MB probe does not require any further modification prior to its use. In a further example, no additional monovalent or divalent salts or additives, such as bovine serum albumin (BSA), are required for the detection assay. In the absence of a target molecule, the MB probe remains in a stable hairpin conformation such that fluorescence from the fluorophore is totally quenched due to the proximity of the fluorophore at one end of the polynucleotide and the quencher at the other end of the polynucleotide. For example, proximity of the carboxyfluorescein (Fam) fluorophore or Rox fluorophore at the 5' end of the MB probe with Dabsyl at the 3' end quenches any fluorescence. In the presence of a target molecule, a portion of the probe hybridizes to a complementary sequence of the target molecule, resulting in the separation of the fluorophore and the quencher and subsequently resulting in the emission of fluorescence from the fluorophore.

Other examples of fluorescence dyes that can be used include SYBR Green I, Eva Green and LG Green.

In examples, the target molecule comprises DNA or RNA. In examples, the target molecule comprises a gene of interest. In an example, the gene of interest may be genes that confer resistance against anti-viral or anti-bacterial treatment, such as treatment with one or more antibiotics. In another example, the gene of interest may be bacterial and viral genes. In a particular example, the genes of interest are associated with human parainfluenza virus (HPIV), such as HPIV1 and HPIV2. In another particular example, the genes of interest are *E. coli* plasmid DNAs.

In an example, the reaction between the detection probe and the target molecule is substantially instantaneous at room temperature, e.g. 30° C. The targets of interest may hybridize with the respective detection probes where the signal emitted is achieved with little noise at an optimal temperature of 30° C. In a further example, there is no need for any incubation of the probe and target to result in a reaction product. There is also no need for any washing before or after the possible reaction.

The device may comprise a cover material to enclose the plurality of wells or channels. The material enclosing the plurality of wells or channels may be transparent. In an example, the plurality of wells or channels is covered by a thin, transparent tape, e.g. MicroAmp™ optical adhesive film which is PCR compatible, DNA/RNA/RNase-free from Applied Biosystems, California, USA. The remaining parts of the device may be made of a translucent material or a non-transparent material.

The device may be made of a material that does not inhibit the binding of the detection probe with the target molecule. The material may be poly(methyl methacrylate) (PMMA), polycarbonate (PC), polypropylene (PP), polyethylene, polyvinyl alcohol, acrylonitrile butadiene styrene or polystyrene. In an example, the device may be compatible with common PCR reagents found on the market, e.g. PCR master mixes from Qiagen, Netherlands (Taq PCR Master Mix Kit), Promega, WI, USA (GoTaq Hot Start Colorless Master Mix) and Invitrogen, CA, USA (Platinum PCR SuperMix).

The microfluidic device as disclosed herein may be comprised in a system, as will be described in detail below.

In an embodiment, there is provided a system comprising: a microfluidic device as disclosed herein, a detection device arranged above or below the microfluidic device for detecting a signal emitted by a possible reaction product comprised in the wells during use.

The detection device may be an optical system. The optical system may comprise a light source and filters that are capable of capturing the signal emitted by the reaction product of the detection probe and the target molecule. The light source and the plurality of wells of the microfluidic device may be positioned concentrically. In an example, each well may receive light of the same intensity, thereby permitting substantially uniform detection of possible reaction products. The light source may be an ultraviolet-visible (UV-Vis) broad band mercury/LED light source and the filters may be excitation, emission and dichroic filters, each having compatible wavelength bands targeting the fluorescent dye used. The light source may be capable of illuminating the plurality of wells of the microfluidic device so that a camera can capture an image of the possible signal emitted. The light source and the filters comprised in the detection device may also be capable of emitting a signal to excite the reaction product to generate fluorescence by the lens and the camera. An example of a suitable camera is the Retiga EXi CCD camera obtained from QImaging, Canada or the Grasshopper2 CCD-based red-green-blue (RGB) camera obtained from Point Grey Research Inc., Richmond BC, Canada, with a 25-mm focus lens obtained from Edmund Optics, NJ, USA. The image captured by the camera may be processed by a processing program. For example, a customized image analysis software from Matlab Image Acquisition Toolbox, The Mathworks Inc., MA, USA, can be used. The processing program may be administered by a processor, such as a computer. In an example, the optical system provides a non-motorized setup for one-shot imaging of emitted signals, such as fluorescence.

Both photodiode and CCD camera can be used for the detection of fluorescence signal of PCR. Since photodiode is a point detector, in order to monitor more PCR wells simultaneously, fiber-optic cables and an optical multiplexer have to be used. This would become increasingly complex and expensive as throughput is further increased. On the other hand, CCD camera detects signal over an area instead of a point, hence the number of PCR wells monitored is irrelevant. However, due to the requirement of some distance between the light source and the PCR wells, and between the PCR wells and the camera, the sensitivity of camera-based detection is generally less than fiber-optic cable-based detection, which suffers little transmission loss over distance. However, this reduced sensitivity is generally not a problem for PCR product detection. With the availability of more sensitive and cost-effective CCD camera, more and more commercial real-time PCR systems may use CCD camera as a detector.

The disclosed system may further comprise a heating element in thermal communication with the plurality of wells.

The heating module may be a Peltier thermoelectric device. The thermoelectric device may comprise a fan, a thermoelectric (TE) heater/cooler, and a TE control kit. The TE control kit may comprise an amplifier and a temperature controller. The TE heater may be powered by the amplifier, which is controlled by the temperature controller. A T-type thermocouple may be mounted on the TE heater to measure the temperature, and may be used as a feedback to the temperature controller. The temperature difference between the TE heater and actual temperature inside the well may be calibrated by measuring the temperature inside the well directly with equal volumes of PCR product. An aluminum cooling heat sink may be attached to the thermoelectric device.

The system may further comprise, connected to a first end of the fluidic channel, fluid sources such as a source comprising a possible target molecule, a sealant source, a washing reagent source, other sources for reagents used for reactions, a positive pressure source, or combinations thereof.

The system may further comprise, connected to a second end of the fluidic channel a vacuum source.

One or more valves may be connected between the fluidic channel, and the sealant source, the source comprising a possible target molecule and the vacuum source.

The various possible connections are as disclosed above.

The vacuum source may be a vacuum pump or a syringe. The positive pressure source may be a positive pressure pump or a syringe.

The vacuum source may be configured to provide a suitable volume of vacuum as appropriate considering the size of the microfluidic device, the common fluidic channel, the isolation channel and/or the wells. The vacuum volume may be chosen to achieve an appropriate speed of the filling step (i) described below. In an example, for individual well volumes of about 3 µL, the vacuum source may be configured to provide a vacuum volume of between about 1 to 22 mL, or between about 2 to 22 mL, or between about 3 to 22 mL, or between about 4 to 22 mL, or between about 5 to 22 mL, or between about 1 to 20 mL, or between about 1 to 15 mL, or between about 5 to 15 mL, for filling step (i). Alternatively, a vacuum of about −50 kPa to about −100 kPa may be pulled for filling step (i). If the vacuum volume applied during step (i) is too high, air bubbles may form within the microfluidic device, thereby reducing the volume of sample available for reaction. Air bubbles may also affect the reaction results. Further, at high filling velocity, flow turbulence could be generated, resulting in air bubbles trapped within the liquid. If the vacuum applied during step (i) is too low, the time taken to fill all of the wells may be inconveniently long. Some wells may also not be filled fully.

In an example, the disclosed device and system may be configured to provide a liquid filling rate as high as 8 ms/well, while preventing drawbacks faced in the prior art. The disclosed device and system may provide a faster method of conducting reactions.

The vacuum source may be configured to provide a vacuum flow rate of about 10 to 100 μl/min, or about 30 to 70 μl/min, for filling step (ii) described below. It should be noted that the vacuum source may be configured to provide any other vacuum flow rates falling within this range.

Figure 4A:
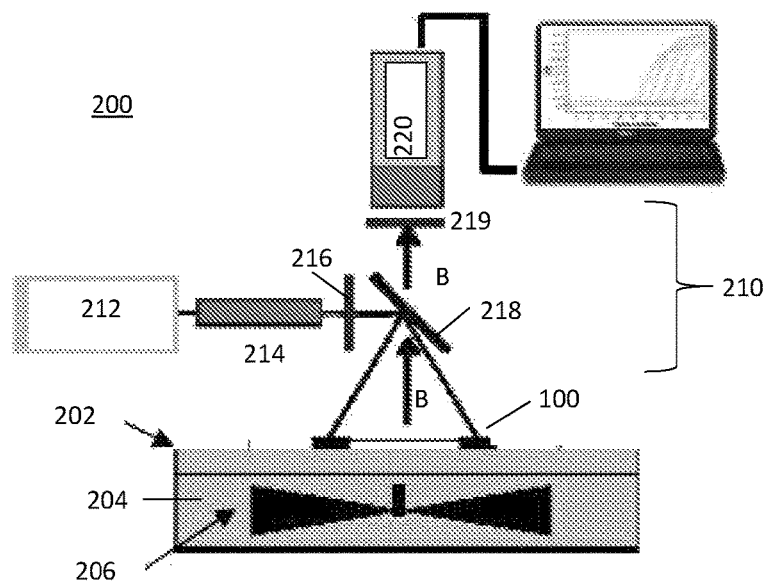
FIG. 4a shows a schematic diagram of a system 200 in accordance with an embodiment of the present disclosure. System 200 comprises, among others, PCR device 100, heating element 202 and optical system 210.

A schematic diagram of an example of the disclosed system in accordance with an embodiment of the present disclosure is shown in FIG. 4a. In this example, system 200 comprises PCR device 100 contacting heating element 202. Heating element 202 comprises a heat sink 204 and fan 206. System 200 also comprises an optical system 210. Optical system 210 comprises a light source 212. Light from light source 212 is transmitted via an optical fiber 214 and filtered by an excitation filter 216 to generate an excitation beam. The beam is reflected by a mirror 218 to laterally excite the PCR device 100 located vertically below. The light emitted from the samples in the PCR chip 100 along arrow B is filtered by an emission filter 219 to generate a fluorescence signal. The signal is focused by a compact lens (not shown) with a fixed focal length. The focused light is then detected by a cooled CCD camera 220 and the light intensity over the entire chip 100 is obtained by analyzing the images captured at certain time points by the camera.

In instances, the disclosed system can not only be used alone, but also as part of an integrated system. An exemplary integrated system is disclosed in U.S. Pat. No. 8,343,443 B2.

Figure 13:
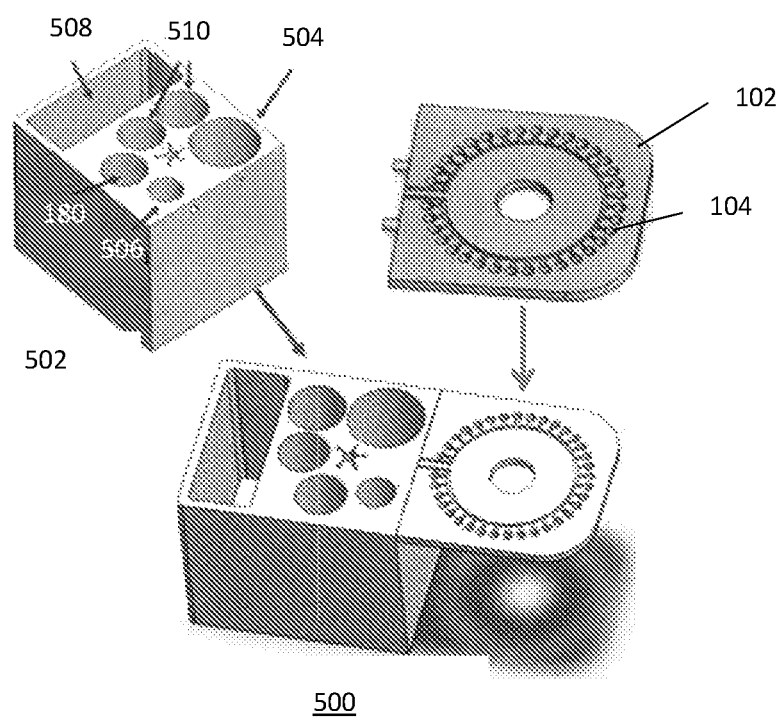
FIG. 13 shows an exploded view of an integrated all-in-one molecular diagnostic device 500 in accordance with an embodiment of the present disclosure comprised of a PCR chip 102 and a sample preparation cartridge 502.

FIG. 13 provides an exploded view of an integrated all-in-one molecular diagnostic device 500 comprised of a PCR chip 102 and a sample preparation cartridge 502. The sample preparation cartridge 502 prepares the target molecules, such as DNA/RNA or protein from raw samples 504 (e.g. blood and nasal swab). The sample preparation cartridge 502 also comprises a channel for sealant 180 and channels for waste 508 and wash reagents 510. The sample preparation cartridge 502 and PCR chip 102 are fitted into the integrated cartridge 500. Once fitted, eluted solution 506 containing the target molecules is transferred to the Omega-shaped chip 102, and introduced into the individual wells 104, which have been pre-loaded with molecular probes. Depending on the application, a heater may be needed for heating the PCR mixture in the chip wells. A detection device, such as CCD camera or photo detector, may be required for measuring the optical signal emitted from the wells.

Methods of using the disclosed device and system are described in detail below.

In an embodiment, there is provided a method of detecting at least one target molecule from a liquid sample using the system as disclosed herein, wherein the method sequentially comprises: (i) filling the plurality of wells with the liquid sample from the source comprising the target molecule; (ii) filling the common fluidic channel with the sealant from the sealant source; (iii) allowing a reaction between the detection probe and the target molecule to take place in the plurality of wells; (iv) detecting a signal emitted by the reaction product.

Step (i) may comprise pulling a vacuum from the vacuum source for a predetermined duration while the fluidic channel is disconnected from the source comprising the possible target molecule; and connecting the source comprising the possible target molecule to the first end of the fluidic channel while the vacuum source is connected or disconnected. In instances, air that may be present within the microfluidic device, such as in the plurality of wells, isolation channel and/or common fluidic channel, may be removed. In instances, in the example where the vacuum source is disconnected after air removal, liquid sample from the source comprising the possible target molecule may be able fill the plurality of wells due to the vacuum remaining within the microfluidic device. In the example where the vacuum source is connected after air removal, the speed of step (i) may be further increased. A reagent flow stopper may be provided before the vacuum source to prevent liquid sample from contacting the vacuum source.

Alternatively, step (i) may comprise pulling a vacuum from the vacuum source while the first end of the fluidic channel is connected to the source comprising the possible target molecule. In instances, air that may be present within the microfluidic device, such as in the plurality of wells, isolation channel and/or common fluidic channel, may be removed, and at the same time, liquid sample from the source comprising the possible target molecule may be able fill the plurality of wells due to the vacuum pulled. A reagent flow stopper may be provided before the vacuum source to prevent liquid sample from contacting the vacuum source.

The plurality of wells may be sequentially filled in step (i). The filling volume of the wells may be insensitive to the strength of vacuum pulled. Hence, step (i) of the disclosed method may be able to yield consistent results. Further, step (i) may fill the plurality of wells in a substantially equal amount.

The disclosed method may further comprise, after step (i) and before step (ii), the step of disconnecting the source comprising the possible target molecule from the fluidic channel; and pulling a vacuum from the vacuum source for a predetermined duration to remove excess liquid sample in the fluidic channel. In an example, excess liquid sample may be removed from the fluidic channel so that detection of a possible reaction product may occur only in the wells. In a further example, detection of false results may be prevented.

Step (ii) may comprise pulling a vacuum from the vacuum source for a predetermined duration while the fluidic channel is disconnected from the sealant source; and connecting the sealant source to the first end of the fluidic channel while the vacuum source is connected or disconnected. In instances, liquid sample that may be remaining within the common fluidic channel may be removed. In instances, in the example where the vacuum source is disconnected after sample removal, sealant from the sealant source may be able fill the common fluidic channel due to the vacuum remaining within the microfluidic device. In the example where the vacuum source is connected after sample removal, the speed of step (ii) may be further increased. A sealant flow stopper may be provided before the vacuum source to prevent sealant from contacting the vacuum source. In an example, the sealant prevents sample from evaporating due to the temperature used during the reaction. Furthermore, the sealant isolates the sample within each well, thereby preventing cross-contamination between adjacent wells.

The sealant may be any type of substance that can at least partially block or prevent leakage of the liquid in the well to effectively isolate the liquid in the well. By "isolate", it is meant that a particular species or substance is separated from a mixture, sample or biological specimen. In instances, liquid in the well after isolation may not be lost to the environment, e.g. by evaporation. In instances, after isolation, the liquid contained in each well will not contaminate liquid in other wells. The occurrence of stray signal emission leading to false-positive emission readings may also be reduced. In an example, there is no occurrence of false positives or false negatives. By "effective", it is meant that the liquid in the well, including the liquid in the isolation channel, is sufficiently separated from the mixture, sample or specimen outside the well, e.g. in the common fluidic channel. The sealant may be any type of material that has a lower rate of vaporization than the liquid in the well. The sealant may be any type of material that has a boiling point well above the liquid in the well so as to remain as stable liquids at the highest operating temperature of the method of use and to prevent the transmission of water vapor. The sealant may be any type of material that is immiscible with the liquid in the well. The sealant may be any type of material that does not allow vapor of the liquid in the well to pass through. The sealant may be silicone oil, wax, polymers, gelatin, gum, starch, or a derivative thereof.

In an example, the sealant may be liquid wax. The term "wax" as used herein includes naturally occurring fatty acid esters such as carnauba, candelilla, beeswax, etc., mineral oil and other organic materials which have the physical character of waxes, such as polyethylenes, paraffins, ozokerites, etc. Paraffin wax is generally used to define hard, crystalline wax commonly obtained from petroleum distillates, derived from mineral oils of the mixed base or paraffin base type and may include materials such as higher boiling distillate waxes and microcrystalline wax.

Alternatively, step (ii) may comprise pulling a vacuum from the vacuum source while the first end of the fluidic channel is connected to the sealant source. In instances, sample that may be present in the common fluidic channel may be removed, and at the same time, sealant from the sealant source may be able fill the common fluidic channel due to the vacuum pulled. A sealant flow stopper may be provided before the vacuum source to prevent sealant from contacting the vacuum source.

To increase the rate of filling steps (i) and/or (ii), sealant may be pumped from the sealant source into the first end of the fluidic channel and/or the possible target molecule may be pumped from its source into the first end of the fluidic channel. The positive pressure may be generated from a syringe containing the possible target molecule, whereby the plunger is pushed inwards to pump the possible target molecule into the first end of the fluidic channel. The positive pressure may be generated from a syringe containing the sealant, whereby the plunger is pushed inwards to pump the sealant into the first end of the fluidic channel.

The vacuum volume of the vacuum generated in step (i) may be as disclosed herein. For example, the vacuum volume of the vacuum generated in step (i) may be between about 5 and 22 ml.

The removal of excess liquid sample in the fluidic channel may be conducted at a rate as disclosed herein. For example, the removal of excess liquid sample in the fluidic channel may be conducted at a rate of between 30 and 70 µl/min.

In an example, the method of operating the system of FIG. 3 in accordance with embodiments of the present disclosure will now be described, with reference to FIG. 3.

Step 1: Valve 142 is positioned at 142*b* and valve 146 is positioned at 146*a*. Pump 160 is at its zero volume position as illustrated. When the plunger 162 starts moving outwards along the direction of the arrow, the air originally contained in the fluidic channel 106, the isolation channels 108 and the wells 104 is sucked out and transported through the reagent stopper 158 to the pump 160. The reagent stopper 158 and the sealant stopper 156 are fabricated from a highly hydrophobic membrane with small holes to stop liquid transfer, but allow gas to pass through.

Step 2: Valve 142 is switched to position 142*a*. Now, the reagent is drawn from the reagent container 170 into the fluidic channel 106 and individual wells 104 by the vacuum generated from Step 1. Once all the wells are filled with reagent, the extra reagent reaches the reagent stopper 158 and stops there. Signal from the pressure detector 170 indicates the end of the filling process, and stops the pump from working.

Step 3: Valve 146 is switched to position 146*b* to release the vacuum in the pump.

Step 4: Valve 144 is positioned at 144*b*, and valve 146 is switched to position 146*c*. Now the pump 160 moves slowly from its zero volume position outwards, and the reagent remaining in the fluidic channel 106 is gently removed.

Step 5: Valve 144 is switched to position 144*a* and valve 146 is switched to position 146*d*. The sealant passes through the fluidic channel 106 to seal all the individual wells 104. Once the sealant reaches the sealant stopper 156, it stops there and the sealing process is completed.

In an alternative embodiment, instead of pulling a vacuum, positive pressure may also be used as the driving force for chip filling and sealing. For this purpose, there would be no need to generate the vacuum in Step 1. In this case, the pressure exerted on the reagent container pushes the reagent to flow into the fluidic channel and then the isolation channel and into the well. An additional exit may need to be created in the wells to allow the air originally in the wells to escape. For example, the top covering tape can be drilled with small orifices, each corresponding to one well. Alternatively, the bottom covering tape can be replaced with a gas-permeable membrane with small pores. In the two cases, air can get away from the orifice or pores, but the strong surface tension would help to prevent liquid leakage. After the wells are filled, Step 4 and Step 5 may then be conducted to seal and isolate the reaction wells. The reagent sealed in the wells is then ready for further reactions, e.g. PCR amplification and detection.

The disclosed device, system and method may be useful to conduct polymerase chain reactions (PCR). In an example, the disclosed device, system and method may be useful to conduct polymerase chain reactions which involve temperatures of less than 95° C., less than 90° C., less than 85° C., or less than 80° C. Depending on the application, bubbles may form in the wells at reaction temperatures of 80° C. or more. In an example, the disclosed device, system and method may be useful to conduct isothermal polymerase chain reactions. As the name suggests, isothermal PCR is conducted at a single temperature and does not require thermal cycling needed in conventional PCR methods. As it does not involve any thermal cycling processes, isothermal PCR systems, such as the disclosed device and system, allow for a simplified design and much lower energy consumption. There are about eight types of isothermal PCR methods, including the most commonly used nucleic acid sequence based amplification (NASBA), loop-mediated isothermal amplification (LAMP), helicase-dependent amplification (HDA), rolling circle amplification (RCA), and strand displacement amplification (SDA). In another example, the disclosed device, system and method may be useful to conduct asymmetric polymerase chain reactions. In yet another example, the disclosed device, system and method may be useful to conduct antibody assays, such as enzyme-linked immunosorbent assays, or molecular diagnostic applications.

An example of an isothermal PCR amplification process is NASBA, which is a continuous process. It works under a relatively low temperature of 41° C., which makes it very suitable for use with a low-power-consumption hand-held device, such as the disclosed microfluidic device. NASBA amplification processes mimic the retroviral RNA replication without the need for thermal cycling. During the amplification, NASBA uses three enzymes, reverse transcriptase, R Nase H and T7 DNA-dependent RNA polymerase. In an example, NASBA has a high amplification factor. For example, the reaction can produce about one billion complimentary RNA molecules in 1.5 h using two primers specific to the target RNA. Real-time NASBA can be achieved by using molecular beacons.

Another example of an isothermal PCR amplification process is helicase-dependent amplification (HDA), which is based on the natural mechanism of DNA replication fork. The HDA process can work at a single temperature of 65° C. HDA may also have a high amplification factor. For example, the IsoAmp tHDA kit (New England Biolabs (Beverly, USA)) can amplify a short DNA sequence of 70 to 130 bp. Successful tHDA amplifications have been achieved on products as short as 85 bp, and as long as 129 bp.

Thus, in an example, the target molecule is the reaction product of an amplification reaction. An amplification reaction results in an increase in the concentration of a nucleic acid molecule relative to its initial concentration by a template-dependent process. The term "template-dependent process" refers to a process that involves the template-dependent extension of a primer molecule. Amplification methods include, but are not limited to polymerase chain reaction (PCR), DNA ligase chain reaction and other amplification reactions well known to persons skilled in the art. The components of an amplification reaction include reagents used to amplify a target nucleic acid, for example, amplification primers, a polynucleotide template, deoxyribonucleotide triphosphate, polymerase and nucleotides. In a particular example, the target molecule is the reaction product of an isothermal polymerase chain reaction.

The disclosed device and system may provide multiple wells for the detection of multiple targets. In embodiments, the well arrangement in a circular shape facilitated the uniform distribution of light intensity to all the wells from a point light source. The disclosed method may provide rapid filling of the wells with liquid by applying vacuum to the device and system as the driving force for liquid flow. In an example, a single well can be filled within 8 ms, and uniform filling volume for different wells can be attained. The performance of the device and system has been successfully demonstrated in processes including NASBA isothermal PCR for RNA samples from HPIV virus, and HDA isothermal PCR for target DNA from E. coli.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1

Preparation of Chip

The chip design was generated using the CAD software Solidworks™ (Dassault Systèmes SolidWorks Corp., France). The polycarbonate substrate comprising holes was then fabricated using a computer numeric controlled (CNC) machine (WHITS Technologies, Singapore). The fabricated PC substrate was later soaked in 0.2% detergent (Decon 90, Decon Lab Ltd., UK) solution for 12 h, followed by rinsing thoroughly with de-ionized water so as to remove any oil contamination from the CNC machining process. Next, the chip was soaked in 3% $H_2O_2$ (MGC Pure Chemicals, Singapore) for 12 h, rinsed with 0.1% diethyl pyrocarbonate (DEPC) (Sigma-Aldrich, Singapore) to remove RNases and DNases, and oven-dried at 60° C. for 6 h. Pipette tips (volume: 20 µL) were cut into segments of 7 mm in length for use as the inlet and outlet tubes and were glued to the two holes at the ends of the fluidic channel. Optical adhesive films (MicroAmp™, Applied Biosystems Inc., MA, USA) were laser-cut into the desired size using a 40-W $CO_2$ cutting system (Helix 40, Epilog, CO, USA) under 20% laser power, and then applied to the top and bottom surfaces of the polycarbonate substrate.

Example 2

The chip from Example 1 was used in this example. A schematic diagram of the chip is shown in FIG. 2a, which is referred to in this example. The operation of the chip was as follows.

Figure 2B:
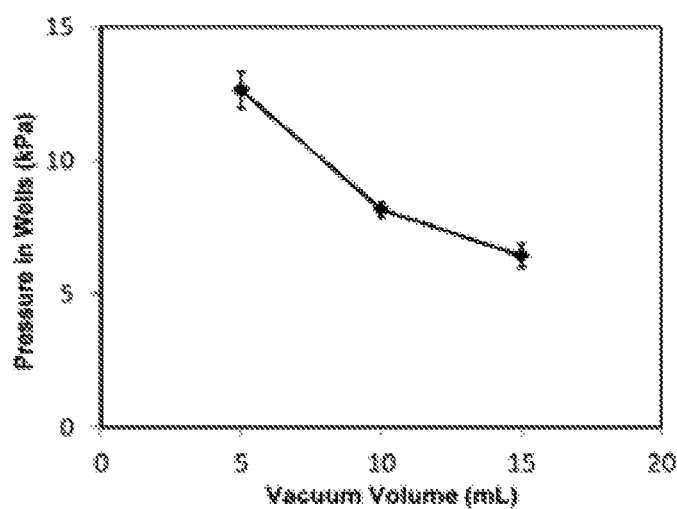
FIG. 2b shows a graph of the pressure in the wells of the device of FIG. 2a corresponding to the vacuum volume of syringe pump 160, referred to in Example 2.

Step 1. The vacuum syringe 160 was set to its zero volume. The inlet pinch valve 152 was closed while the outlet valve 154 was opened. The plunger 162 of vacuum syringe 160 was moved outwards to generate a vacuum for removing air from the channel and the wells of chip 100. The target volume of the syringe was set to 2.5, 5, 10 or 15 mL, depending on the vacuum level needed for the subsequent step of filling the wells. The actual pressure in the wells corresponding to the vacuum volume of syringe pump was calibrated, as shown in FIG. 2b.

Step 2. Valve 152 was opened. Due to the vacuum generated in the common fluidic channel and the wells in Step 1, the PCR mixture moved into the fluidic channel of chip 100 and filled the wells one by one, sequentially, within 0.5 s. Once the PCR mixture reached the outlet of chip 100, valve 154 was closed to isolate the chip 100 from the vacuum in the syringe pump 160. The filling process continued due to the vacuum remaining in the common fluidic channel and the wells. After about 10 s when all the wells were completely filled, Valve 152 was also closed.

Step 3. The Eppendorf tube 170 with PCR mixture was removed. At the same time, the vacuum in the syringe pump 160 was released. Valves 152 and 154 were then opened. The syringe pump 160 was started and ran at a slow speed of 50 μL/min. As a result, the PCR mixture remaining inside the common fluidic channel was gently drawn out of the chip 100. After that, another Eppendorf tube (not shown) containing 100 μL of liquid wax (Bio-Rad, Singapore) was attached to the inlet of the chip 100. With the pumping from the syringe 160, the silicone oil gradually filled the fluidic channel, and its immiscibility with water helped to effectively seal all the individual wells in the chip 100.

To study the details of the PCR mixture filling/sealing process, a high-speed video camera (MotionPro X4, DEL Imaging Systems, USA) was employed to monitor the above process at a recording rate of 600 frames/s. Deionized water was used to simulate the PCR mixture solution, with the addition of ink to improve the image contrast for easier observation. The temporal information could be obtained from the time point when the corresponding frame was obtained.

The above steps were followed to investigate the filling/sealing process of the PCR chip.

The outlet of the chip was connected to a 10-mL syringe that was controlled by a motorized syringe pump. The plunger of the syringe was pushed inwards to zero volume. Prior to the start of sample loading, the inlet and outlet pinch valves were set at the "close" and "open" positions, respectively. When the plunger began to be moved outwards, the air originally sealed in the chip channel and wells (ambient pressure=$P_0$, volume=$V_0$) expanded. When the air volume was increased to V, the pressure P inside the channel/wells could be calculated from the ideal gas law:

$$P=P_0 V_0/(V_0+V)$$

In this example, the syringe vacuum volume V was set at 1-10 mL, which generates a vacuum of −79.9 to −89.9 kPa. The vacuum was maintained for 10 s for pressure stabilization before the inlet pinch valve was opened. After the inlet valve was opened, the PCR mixture in the reservoir, which was subjected to the pressure difference of ($P_0$−P), moved along the fluidic channel and entered every single reaction well. FIG. 5a shows the sample loading snapshots from a video taken with the high-speed video camera. It can be seen that air inside the fluidic channel and reaction wells was sucked out by the external syringe, and then the PCR mixture was introduced to fill the fluidic channel and reaction wells. The wells were filled sequentially—the ones near the inlet were filled earlier than those near the exit. For a 35-well PCR chip, the filling process was completed within 300 ms for a vacuum volume of 10 mL.

Figure 5B:
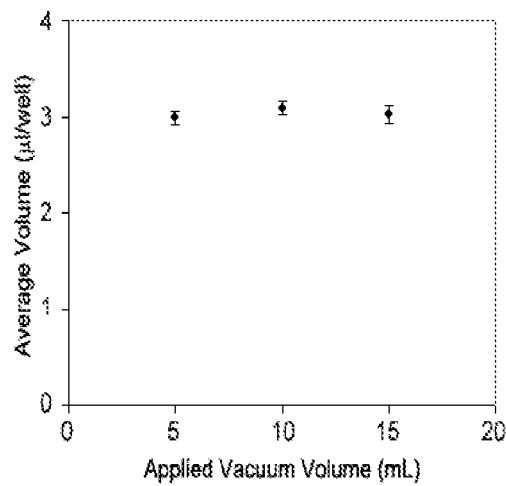
FIG. 5b shows a graph relating the average filling volume per well with the applied vacuum, referred to in Example 2.

The dependence of the average filling volume per well on the applied vacuum is shown in FIG. 5b. The volume of liquid in each well was calculated by dividing the weight measured from a precision weight balance (AB204-S, Mettler Toledo, USA) with the liquid density. The filling volume was found to be insensitive to the range of vacuum volumes optimized for this application (5-15 mL). For example, the filling volumes corresponding to the vacuum volumes of 5, 10 and 15 mL were 3.02, 3.11 and 3.06 μL, respectively. These values were very close to the theoretical liquid volume in a fully filled well of 3.14 μL calculated from the well dimensions (diameter=2.0 mm and depth=1.0 mm), indicating that the wells were fully or almost fully filled in the sample loading process.

Figure 5C:
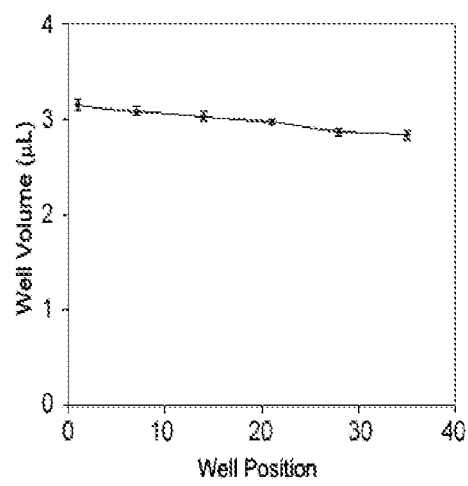
FIG. 5c shows a graph relating the volume filled in different wells with the well position along the fluidic channel, referred to in Example 2.

FIG. 5c shows the volume filled in different wells along the fluidic channel. The first well has a slightly higher filled volume of 3.09 μl, while the last well has a filled volume of 2.994 Their difference in filled volume was 3.3%, indicating good uniformity in the filling of different wells. The filled volume only decreased very slightly for the wells along the flow channel. This minor difference could be due to a gradually reduced vacuum level during the filling process, i.e. the downstream wells might have been slightly less filled under a slightly lower vacuum level.

Since vacuum can be easily applied to microfluidic systems, this example shows that the disclosed PCR mixture filling approach is expected to be more effective than prior art methods, which has been confirmed through the following experiments.

Example 3a

Optimization of the Applied Vacuum Level

The effectiveness of the disclosed PCR mixture filling approach in Example 2 was confirmed in this example.

One parameter important for vacuum filling is the vacuum level applied to drive the fluid. Inadequate vacuum slows down the filling process. It could further result in the significant trapping of air in the reaction wells, which might lead to the failure of the PCR process due to expansion of the trapped air at high temperatures, causing problems in amplification and detection. On the other hand, if the vacuum level is too high, bubbles might form as a result of water evaporation at low pressures, which would negatively affect the filling process by blocking the fluidic and isolation channels.

To obtain the optimal vacuum level, vacuum volumes of 1-22 mL were tested for sample loading, and the corresponding filling quality was examined and compared.

Figure 6A:
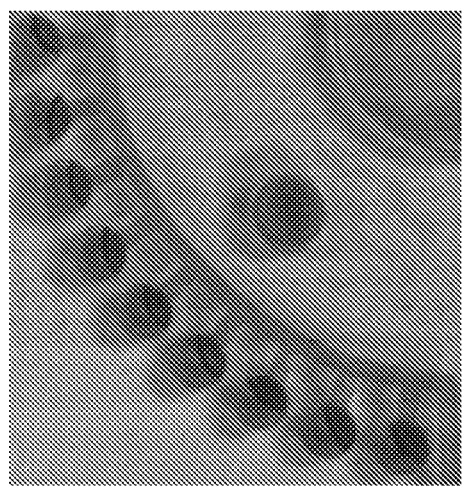

FIG. 6a shows a photo of the PCR chamber when an insufficient vacuum volume of less than 5 mL was used. As shown in FIG. 6a, several PCR chambers were not filled fully as indicated by the arrow.

Figure 6B:
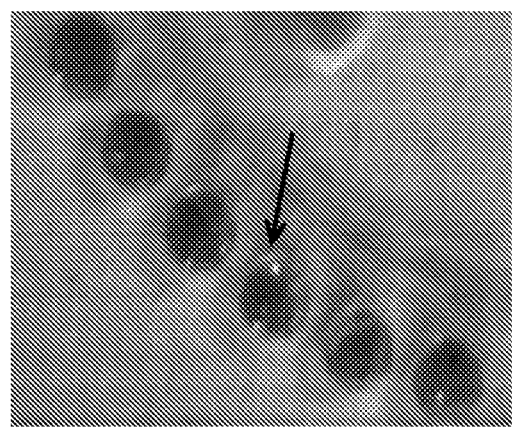
FIG. 6b shows a photo of the PCR chamber when a vacuum volume of 22 mL was used.

On the other hand, FIG. 6b which shows a photo of the PCR chamber when a vacuum volume of 22 mL was used, evidences that bubbles form easily inside the fluidic channel and the wells (indicated by the arrow). In this case, some of the PCR mixture solution may evaporate and PCR mixture solution may be lost. Moreover, the high filling velocity also generates flow turbulence, and as a result, air may be trapped as bubbles within the filling liquid. Accordingly, it is shown in this example that a suitable vacuum volume would be in the range of 5-15 mL.

Example 3b

Optimization of Sealing of the Reaction Well

Figure 7:
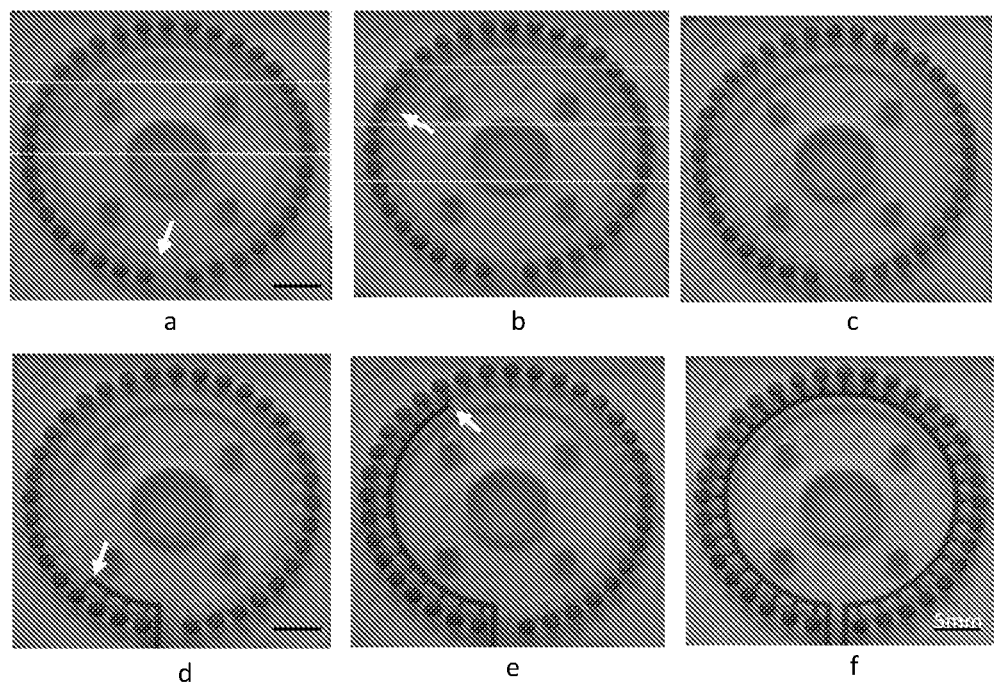
FIG. 7 shows photos of the progress of the sealing process in Example 3b.

Liquid wax was investigated for sealing and isolating each PCR well. FIG. 7 shows photos of the progress of the sealing process in this example.

Referring to FIG. 2a, after the PCR mixture was loaded into the wells 104, the outlet pinch valve 154 was closed and the vacuum in the syringe pump 160 was released to atmosphere. Next, the pinch valve 154 was opened again, and the syringe pump 160 slowly pumped away the PCR mixture remaining in the fluidic channel 106 at a flow rate of 50 μL/min.

FIGS. 7a to 7c show the progress of the removal of PCR mixture. After the PCR mixture was fully removed, liquid wax was introduced from the inlet and filled the void space in the fluidic channel. The white arrows show the interfaces between the PCR mixture and air in the fluidic channel. FIGS. 7d to 7f show the progress of the introduction of liquid wax. The white arrows show the position of the liquid wax in the fluidic channel. The PCR mixture was sealed inside the reaction wells by the liquid wax, unable to evaporate and escape from the Omega chip. Both the inlet and outlet valves were then closed, and the entire chip was subjected to PCR thermal cycling.

Example 4

Real-Time PCR System

A real-time PCR system for characterizing the PCR chip from Example 1 was constructed and tested in this example.

An exemplary PCR system is shown in FIG. 4a. Referring to FIG. 4a, a Peltier thermoelectric device (TEC) 202 was used to generate the required temperature for the PCR reaction. An aluminum cooling heat sink 204 was attached to the backside of the TEC 202. Furthermore, a small cooling fan 206 was attached to the aluminum block to enhance the cooling effect. Plate temperature was measured by a 2.252-k$\Omega$ resistive temperature detector (RTD) (Cat. #201347, FerroTec, USA). A digital temperature controller (FTC100) and an H-bridge amplifier (FTA600) from Ferro-Tec were used for the feedback temperature control.

An optical system 210 was developed for the detection of fluorescence of SYBR Green I/Eva Green in the real-time PCR system. The light from a solid state switchable light source 212 (Lumencor, Spectra Light Engine, Lumencor Inc., Beaverton, Oreg., USA) was transmitted via an optical fiber 214 (400 μm, 0.75 m UV-SR, Ocean Optics), and filtered by an excitation filter 216 (D480/30X, Chroma Technology Co., USA) to generate the 480-nm blue excitation beam. The light beam was reflected by a mirror 218, and laterally excited on the detection PCR chip 100 that was located 10 cm vertically below it. The light emitted from the samples in the PCR chip 100 was filtered by an emission filter 219 (HQ535/50M, Chroma Technology Co., USA) to generate the fluorescence signal at 520 nm. This signal was focused by a compact lens with a fixed focal length (Cat. 59871, Edmund Optics, USA). The working distance between the lens and the PCR chip 100 ranged from 15 to 25 cm. The focused light was then detected by a cooled CCD camera 220 (Retiga EXi, QImaging, Canada), and the light intensity over the entire chip was obtained by analyzing the images captured at certain time points by the camera 220.

Figure 4B:
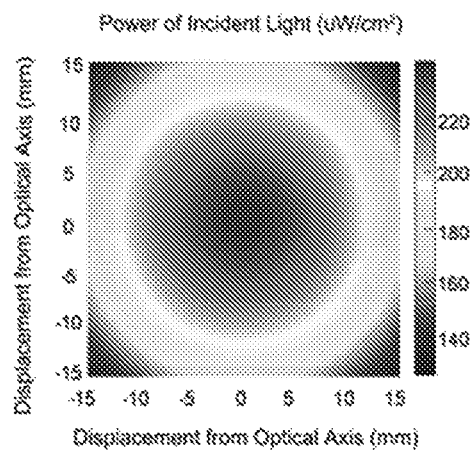
FIG. 4b shows simulation results based on Gaussian normal distribution of light from optical system 210, referred to in Example 4. The plurality of wells of device 100 may be arranged in a complementary manner to the distribution of light.

A power meter (Model 841-PE, Newport Corp., CA, USA) was used to measure light intensity (in μW/cm$^2$) at various lateral displacements from the optical axis. The data (not shown) agreed well with the simulation results based on Gaussian normal distribution (MATLAB, Mathworks Inc., USA) (see FIG. 4b). The distribution of the power of the incident light was axisymmetric around the optical axis, and a sufficiently high intensity could be obtained for displacements ranging from −15 mm to 15 mm, which was comparable to the dimensions of the Omega chip. Given that both the Omega chip and the Gaussian distribution of light intensity were radially symmetrical, it is concluded that each well would receive light of the same intensity when the chip and optical detection were positioned concentrically. This is an important feature of the present optical detection system, which allowed similar sensitivity to be achieved for each well.

Example 5

On-Chip NASBA Amplification for Virus Detection

Nucleic acid sequence based amplification (NASBA) amplification was used to detect two types of human parainfluenza virus (HPIV) on the chip of Example 1.

HPIV is one of the major causes for upper and lower respiratory tract illnesses in pediatric patients, and breaks out annually in winter. There are four recognized serotypes of HPIV: HPIV1, HPIV2, HPIV3 and HPIV4, but only HPIV1 and HPIV2 are commonly found. In this example, HPIV 1 and HPIV 2 were used for testing purposes.

The required reagents for NASBA were adopted from a NucliSens Basic Kit (bioMérieux, UK). They were prepared according to the protocol recommended by the manufacturer before the experiment was conducted. Briefly, 80 μL of reagent diluent was added to one reagent sphere from the kit to make the ready-to-use reagent solution. The ready-to-use KCl solution was prepared by mixing 14 μL of KCl stock solution in the kit with 16 μL of NASBA water. The enzyme solution was prepared by adding 45 μL of enzyme dilution from the kit to one enzyme sphere. The RNA molecules of HPIV1 (Cat. VR-94D) and HPIV2 (Cat. VR-92D) were purchased from the American Type Culture Collection (ATCC) (USA).

Since each well has a volume of 3 μL, filling a 28-well PCR chip requires a total sample volume of 84 μL. Therefore, 120 μL of PCR mixture was prepared for the filling and testing, which comprised 30 μL of virus RNA template, 39 μL of reagent solution, 15 μL of KCl solution, 30 μL of enzyme solution and 6 μL of water.

Primers and molecular beacon probes were purchased from Eurogentec (Cat. NB-PAI01-48 for HPIV1 detection using Fam-Dabsyl molecular beacon, Cat. NB-PAI02-48 for HPIV1 detection using Rox-Dabsyl molecular beacon). The primers were pre-deposited into individual wells during the chip assembly.

The NASBA assay involves a continuous, isothermal process without the need for thermal cycling. The sensitivity of the NASBA assay conducted in the chip was tested in this example using the original virus stock solution, and dilutions by 10 to 10,000 folds. The diluted template was mixed with other components to prepare the 120-μL PCR mixture. To prepare the negative control, water free of DNase and RNase was used instead of the diluted virus sample.

The PCR mixture was introduced to the wells of the Omega chip using vacuum, and then sealed with liquid wax, as previously described. Next, the entire chip was mounted onto the TEC heater, and PCR amplification was run for 1.5 h at 41° C. The image of the chip was obtained with the CCD camera every 5 min.

Figure 8:
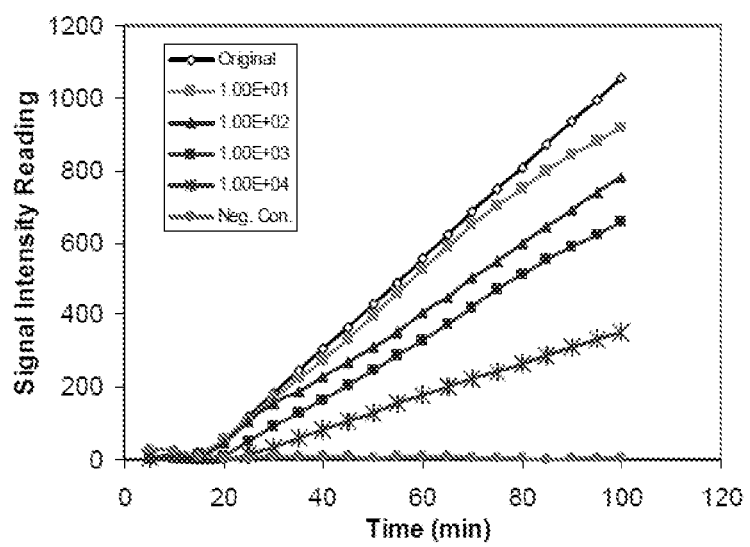
FIG. 8 shows the amplification curves of the original stock RNA sample, its 10× to 10,000× dilutions (i.e. concentrations of 1.00E+01, 1.00E+02, 1.00E+03 and 1.00E+04) and a negative control, referred to in Example 5.

FIG. 8 shows the amplification curves of the original stock RNA sample and its 10× to 10,000× dilutions (i.e. concentration of 1.00E+01, 1.00E+02, 1.00E+03 and 1.00E+04 in FIG. 8) in real-time detection on the Omega chip. After about 20 min of reaction, the fluorescence intensity began to increase almost linearly, except for the negative control. The time-to-positive for the positive amplifications varied from 20 to 30 min. There was a clear relationship between the rate of fluorescence intensity increase and the input template RNA concentration. As expected, a higher RNA concentration led to a faster increase in signal intensity.

Figure 9:
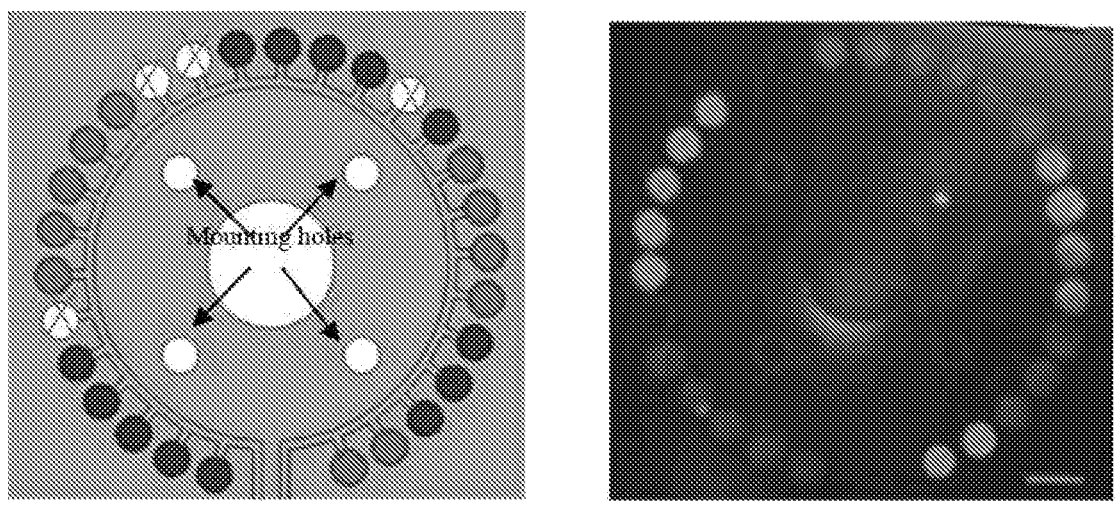
FIG. 9 shows images of the simultaneous end-point detection for HPIV1 and HPIV2 viruses on the Omega PCR array chip, referred to in Example 5.

FIG. 9 shows images of the simultaneous end-point detection for HPIV1 and HPIV2 viruses on the Omega PCR array chip. A color Grasshopper2 CCD-based RGB camera (Point Grey Research Inc., Richmond, BC, Canada) with a 25-mm focus lens was used for this example. A full quad-band filter set (Semrock Inc., Rochester, N.Y., USA) was used as the excitation light filter. As stated above, the wells were preloaded with either Fam-Dabsyl or Rox-Dabsyl molecular beacon. The former displayed a blue color for positive identification of HPIV1, while the latter displayed a red color for HPIV2. A mixture of HPIV1 and HPIV2 samples in 1:1 volume ratio was used as the RNA template in this example.

As seen in FIG. 9, a strong blue fluorescence was observed from the wells deposited with Fam-Dabsyl, and a red fluorescence was seen in the wells with Rox-Dabsyl. The wells without any primer (marked with a cross) did not show any fluorescence signal, confirming that there was no cross-talk between the different wells. This study demonstrated that the Omega PCR array chip could be employed for the simultaneous detection of multiple targets.

Example 6a

Bacteria Culture and Plasmid DNA Preparation for HDA

E. coli (ATCC25922) bacteria used for the isothermal helicase-dependent amplification (HDA) study were obtained from ATCC (USA). They were cultured in the tryptic soy broth (TSB) buffer (BD, USA) contained in a 1.5-mL Eppendorf tube placed on a thermal mixer (Thermal Mixer Comfort, Eppendorf Co., USA) at 41.5° C. After overnight culture, the bacteria were harvested by centrifuge. 10 μL of serially diluted bacteria sample was introduced into a C-Chip (DHC-N01, Incyto Co. Korea) and the image of bacteria was captured by the CCD camera of an optical microscope (IX51, Olympus, USA). The number of bacteria was counted from the image, and the corresponding density was calculated. About 103 to 109 bacteria cells were collected into a 1.5-mL tube for plasmid DNA extraction using the Plasmid Minit Kit (Cat. 12143, Qiagen, Singapore).

According to the user manual from the manufacturer, the extraction included three main steps: (i) bacteria cell lysis and lysate collection, (ii) DNA extraction and purification, and (iii) DNA elution. In the bacteria lysis step, the cell suspension was centrifuged at 8000 rpm for 10 min. After the supernatant was removed, 250 μL of buffer P1 was added to the tube to re-suspend the bacteria. Next, 250 μL of buffer P2 was added and mixed thoroughly by gently inverting the tube five times. After 2 min of incubation, 350 μL of buffer N3 was added and mixed thoroughly by inverting the tube 10 times. After the lysis steps, the solution was centrifuged at 10,000 rpm for 10 min. The supernatant was collected and transferred to a QIAprep spin column for DNA extraction and purification. The DNA extraction was done by spinning the solution at 3,000 rpm for 1 min. The DNA molecules were solid-phase extracted onto the spin column, while the flow-through was discarded. The purification process involved adding 0.75 mL of buffer PE to the column, and centrifuging at 3,000 rpm for 1 min. In the elution process, the column with purified DNA molecules was placed in a clean 1.5-mL tube. 50 μL of buffer PE was added to the tube. After 1 min of incubation, the tube was centrifuged at 3000 rpm for 1 min, and the pure plasmid DNA molecules in the eluted solution were collected for the downstream isothermal HDA PCR amplification.

Example 6b

Real-Time HDA PCR Amplification

HDA is based on the natural mechanism of DNA replication fork. It can work at a single temperature of 65° C.

The IsoAmp tHDA-III kit from New England Biolabs (Beverly, USA) was used for the isothermal PCR amplification detection of E. coli plasmid DNAs prepared in Example 6a. The IsoAmp tHDA kit can amplify a short DNA sequence of 70 to 130 bp. Successful tHDA amplifications have been achieved on products as short as 85 bp, and as long as 129 bp.

The tHDA kit contained the required reagents for the PCR amplification, except the DNA template, forward primer and reverse primer. A tHDA reaction mainly consisted of the following materials: 1× annealing buffer, 25× enzyme mix, 14× dNTP solution, 3-4.5 mM of MgSO4, and 20-50 mM of NaCl. In this example, target M13 gene of the E. coli DNA was amplified. According the sequences of primer 1233 and 1224 (New England Biolabs, USA), the forward and reverse primers were 5'AGCGGATAACAATTTCACACAGGA3' and 5' CGCCAGGGTTTTCCCAGTCACGAC3', respectively.

The IsoAmp tHDA kit did not come with the reporting dye for real-time PCR. Currently, SYBR Green I, Eva Green and LG Green are the most widely used reporting dyes for real-time PCR. Although both Eva Green and SYBR Green could be used, previous studies have shown that the Eva Green has much lower PCR inhibition than other dyes. Hence, Eva Green was chosen as the reporting dye for real-time HDA.

Figure 10:
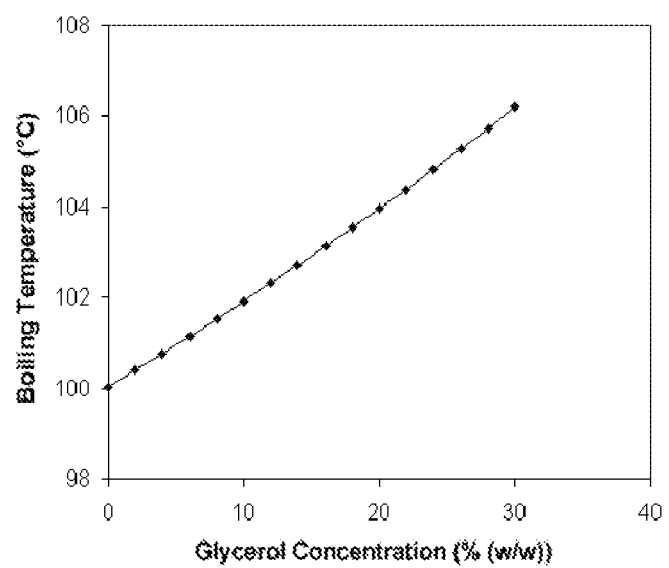
FIG. 10 shows a graph relating boiling temperatures for different glycerol concentrations, referred to in Example 6b.

Although the liquid wax sealing of reaction wells helped to prevent gas from escaping from the chip, it did not eliminate water evaporation inside the wells at high temperatures. To solve this problem, the PCR mixture was pre-mixed with a certain amount of glycerol to reduce the vapor pressure. According to Raoult's law, the vapor pressure of a water/glycerol mixture P can be approximated as, $$P_{(T)} = P_{W(T)} x_W + P_{G(T)} x_G$$

where $P_{W(T)}$ and $P_{G(T)}$ are the vapor pressures of water and glycerol at temperature T, respectively, and $x_W$ and $x_G$ are the mole fractions of water and glycerol, respectively. The molecular weights of water and glycerol are 18 and 92, respectively; the weight percentages of water and glycerol used in experiments can be converted to mole fractions with these molecular weights. Since glycerol has a much lower vapor pressure than water at the same temperature, the above equation shows that the addition of glycerol may decrease the vapor pressure of a PCR mixture. At the boiling temperature, the vapor pressure of the mixture is equal to the ambient pressure of 1 atm. The boiling temperatures calculated for different glycerol concentrations are shown in FIG. 10.

It has been examined that the addition of 5% to 20% (w/w) glycerol did not significantly affect the fluorescence intensity and the PCR CT value. Accordingly, 15% (w/w) of glycerol was added to the PCR mixture in this example. At this concentration, the mixture's boiling temperature was ~103° C.

The forward and reverse primer pairs specific for the target region of the bacteria DNA were preloaded into the wells. The PCR mixture was introduced to the wells of the Omega chip using vacuum, and then sealed with liquid wax, as previously described.

Figure 11:
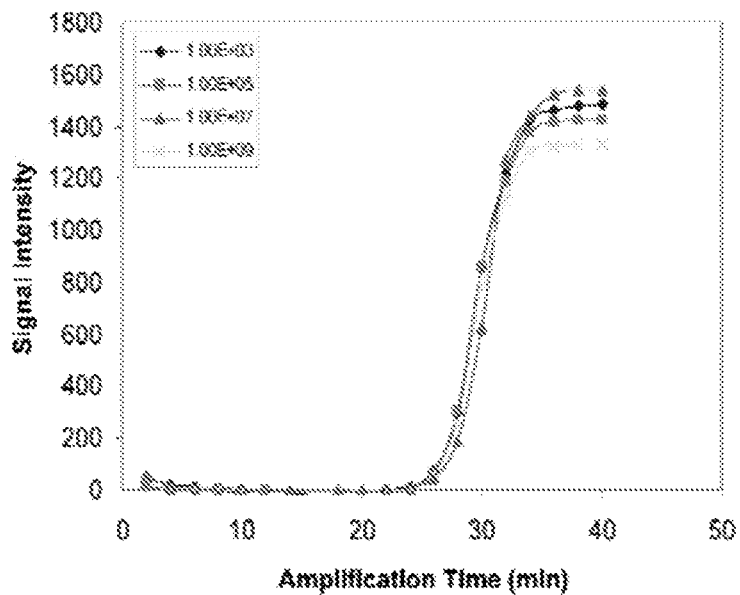
FIG. 11 shows the amplification curves of plasmid DNA extracted from about $10^3$, $10^5$, $10^7$ and $10^9$ bacteria cells, referred to in Example 6b.

Plasmid DNA extracted from about $10^3$, $10^5$, $10^7$ and $10^9$ bacteria cells was introduced to 4 different chips, and subjected to isothermal PCR amplification. The fluorescence signal from individual wells was captured every 2 min. The results are shown in FIG. 11. As seen in FIG. 11, the PCR amplification became very obvious after about 27 min. The time required was not significantly different for extractions from different bacteria concentrations, indicating that HDA might not be suitable for the quantitative detection of E. coli.

Figure 12:
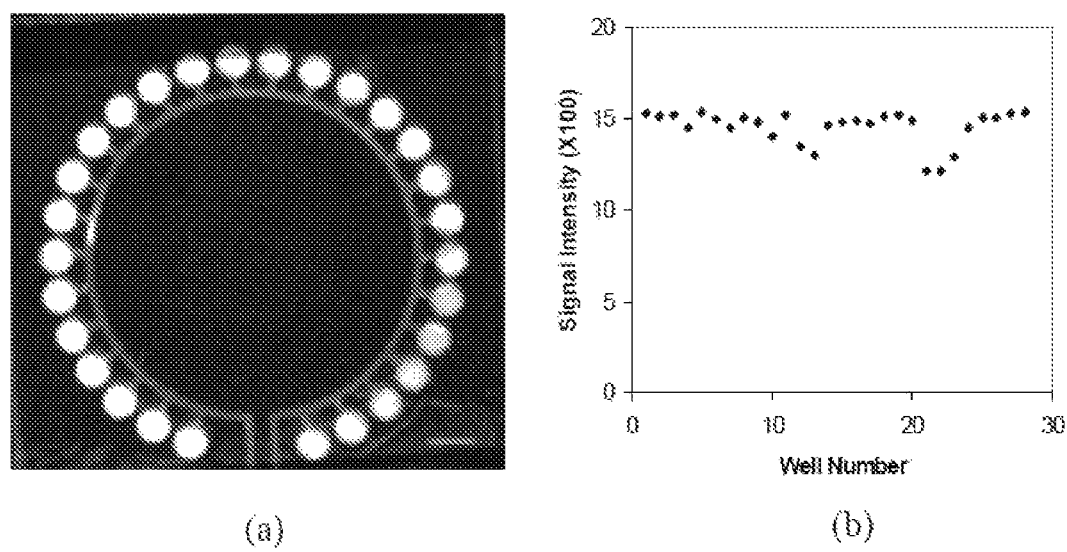
FIG. 12a shows the end-point florescence signals captured after 40 min of HDA at 65° C., referred to in Example 6b.
FIG. 12b shows a graph relating well-by-well signal intensity against well number, referred to in Example 6b.

Uniformity of florescence signal was important in the quantitative detection of genes. In order to check the detection uniformity in the Omega PCR array chip, the same amount of primers was preloaded, and the same PCR mixture was vacuum-filled (including the DNA sample extracted from 109 bacteria cells) into each well. After 40 min of HDA at 65° C., the end-point florescence signals captured is shown in FIG. 12a. Well-by-well signal intensity was quantitatively measured by ImageJ software (NIH, USA) and the measurements were plotted as shown in FIG. 12b. The signal intensity reading for the 28 wells ranged from 1208 to 1533. The average signal intensity for the 28 wells was 1454, and the standard deviation was ±93, which was about 6.3% of the average signal intensity, indicating a fairly uniform distribution in florescence signals amongst the different wells.

What is claimed is:

1. A microfluidic device for PCR amplification comprising:
a plurality of wells, each well comprising one opening to function as both an inlet and an outlet for the well,
wherein each opening is in fluid communication with a common fluidic channel, and wherein
each opening is connected to the common fluidic channel via an isolation channel, and
wherein the plurality of wells are arranged on the device in a radially symmetrical pattern,
wherein a first end of the common fluidic channel is dimensioned to be fluidly connected with one or more of the following sources via one or more connections: a source comprising a possible target molecule, a sealant source, a washing reagent source and other sources for reagents used for polymerase chain reactions or enzyme-linked immunosorbent assays,
wherein a second end of the common fluidic channel is dimensioned to be fluidly connected with a vacuum pump or a syringe; and
wherein one or more liquid flow stoppers are connected between the second end of the fluidic channel and the vacuum pump or the syringe, wherein the stopper comprises holes sized to prevent liquid from passing through, but allow gas to pass through.

2. The device of claim 1, wherein the one or more connections are separately controllable by one or more valves.

3. The device of claim 1, wherein the cross-sectional dimension of the common fluidic channel is between 0.05 and 3 mm by between 0.05 and 3 mm, preferably 0.5 mm by 0.5 mm.

4. The device of claim 1, wherein the volume of each well is independently selected to be between 1 and 50 μl.

5. The device of claim 1, wherein each well comprises a detection probe, optionally wherein the detection probe is capable of forming a reaction product with a target molecule.

6. The device of claim 1, wherein the plurality of wells are in the range of between 2 and 100, or 5 and 100, or 5 and 50.

7. The device of claim 1, wherein the material covering or forming the top and/or bottom of the well is made of an optically transparent material.

8. The device of claim 1, wherein (i) all of the wells are positioned on one side of the common fluidic channel in a common plane, or (ii) a first set of wells are positioned on a first side of the common fluidic channel and a second set of wells are positioned on an opposite side of the common fluidic channel in a common plane as the first side, or (iii) the wells are positioned radially around the common fluidic channel, optionally wherein the isolation channels of opposing wells are located at the same point on the common fluidic channel or at different points on the common fluidic channel.

9. The device of claim 1, wherein the isolation channel of each well is positioned at an angle of 10° to 90° relative to the common fluidic channel.

10. A system for PCR amplification comprising:
a microfluidic device of claim 1 further comprising:
a detection device arranged above or below the microfluidic device for detecting a signal emitted by a possible reaction product comprised in the wells during use.

11. The system of claim 10, wherein the plurality of wells and a light source of the detection device are positioned concentrically.

12. The system of claim 10, further comprising a sealant source connected to a first end of the common fluidic channel.

13. The system of claim 10, further comprising a source comprising a possible target molecule connected to a first end of the common fluidic channel.

14. The system of claim 10, further comprising the vacuum pump or the syringe connected to a second end of the common fluidic channel.

15. The system of claim 12, wherein one or more valves are connected between the common fluidic channel and the sealant source, the source comprising a possible target molecule and the vacuum pump or the syringe, optionally wherein the vacuum pump or the syringe provides a vacuum volume of between 5 and 22 ml.

16. The system of claim 10, further comprising a heating element in thermal communication with the plurality of wells.

17. The system of claim 10, wherein the sealant is liquid wax.

* * * * *